(12) United States Patent
Kramer

(10) Patent No.: US 6,512,381 B2
(45) Date of Patent: Jan. 28, 2003

(54) ENHANCED FINGERPRINT DETECTION

(75) Inventor: Alan Kramer, Berkeley, CA (US)

(73) Assignee: STMicroelectronics, Inc., Carrollton, TX (US)

( * ) Notice: Subject to any disclaimer, the term of this patent is extended or adjusted under 35 U.S.C. 154(b) by 0 days.

(21) Appl. No.: 09/753,344

(22) Filed: Dec. 29, 2000

(65) Prior Publication Data

US 2001/0025532 A1 Oct. 4, 2001

Related U.S. Application Data

(63) Continuation-in-part of application No. 09/475,351, filed on Dec. 30, 1999.

(51) Int. Cl.[7] .............................................. G01R 27/26
(52) U.S. Cl. ....................................... 324/658; 324/661
(58) Field of Search ................................ 324/658, 661; 361/280

(56) References Cited

U.S. PATENT DOCUMENTS

| | | | |
|---|---|---|---|
| 3,493,855 A | 2/1970 | Norwich | 324/61 |
| 3,641,431 A | 2/1972 | Pigage et al. | 324/61 R |
| 3,781,855 A | 12/1973 | Killen | 340/146.3 E |
| 3,873,927 A | 3/1975 | Overall | 328/4 |
| 3,967,310 A | 6/1976 | Horiuchi et al. | 357/54 |
| 4,016,490 A | 4/1977 | Weckenmann et al. | 324/61 R |
| 4,096,758 A | 6/1978 | Moore | 73/718 |
| 4,161,743 A | 7/1979 | Yonezawa et al. | 357/54 |

(List continued on next page.)

FOREIGN PATENT DOCUMENTS

| | | |
|---|---|---|
| EP | 0 343 580 B1 | 11/1989 |
| EP | 0 397 244 A2 | 11/1990 |
| EP | 0 397 244 A3 | 11/1990 |
| EP | 0 397 244 B1 | 11/1990 |

(List continued on next page.)

OTHER PUBLICATIONS

Wolffenbuttel et al., "Integrated Tactile Imager With An Intrinsic Contour Detection Option," *Sensors and Actuators*, 16:141–153, 1989.

Sarma et al., "Capacitance–Type Blade–Tip Clearance Measurement System Using a Dual Amplifier with Ramp/DC Inputs and Integration," *IEEE Transactions on Instrumentation and Measurement* 41(5):674–678, Oct. 1992.

(List continued on next page.)

*Primary Examiner*—Christine K. Oda
(74) *Attorney, Agent, or Firm*—David V. Carlson; Lisa K. Jorgenson

(57) ABSTRACT

An enhanced fingerprint sensing circuit in which a voltage change is applied to the body during sensing. When the person's fingerprint is being sensed, the person's body is in contact with an electrical terminal. When the sensing occurs, the voltage on the electrical terminal changes, which changes the voltage on the person's body. The pattern of the fingerprint performs two functions in the sensing circuit. In addition to being a plate of a capacitor whose distance is being sensed, it is now a source of input charge as well. The electrical effect on the cell of a voltage change on a person's finger is different at a ridge than at a valley in the fingerprint sensing circuit. Thus, the input capacitance to the sensing circuit is variable, depending upon whether a ridge or a valley is present. The sensing circuit also detects a change in its own capacitance based on the presence of a ridge or a valley. In summary, the person's body acts as the input capacitor to provide a variable charge transfer for the input capacitance and at the same time performs the function of being a variable sensing capacitor value for the capacitive sensor. The fingerprint sensor is thus very sensitive and can detect a person's fingerprint even if a protective layer, such as plastic, wax paper or the like is over the sensor. In addition, if the person is wearing a thin glove, such as a latex glove, the fingerprint patterns can still be sensed.

22 Claims, 11 Drawing Sheets

U.S. PATENT DOCUMENTS

| | | | |
|---|---|---|---|
| 4,183,060 A | 1/1980 | Barnette et al. | 358/128 |
| 4,353,056 A | 10/1982 | Tsikos | 340/146.3 E |
| 4,394,773 A | 7/1983 | Ruell | 382/4 |
| 4,428,670 A | 1/1984 | Ruell et al. | 356/71 |
| 4,429,413 A | 1/1984 | Edwards | 382/4 |
| 4,513,298 A | 4/1985 | Scheu | 346/140 R |
| 4,547,898 A | 10/1985 | Tsikos | 382/4 |
| 4,571,543 A | 2/1986 | Raymond et al. | 324/425 |
| 4,577,345 A | 3/1986 | Abramov | 382/4 |
| 4,626,774 A | 12/1986 | Regtien | 324/61 R |
| 4,641,350 A | 2/1987 | Bunn | 382/4 |
| 4,656,871 A | 4/1987 | Czarnocki | 73/724 |
| 4,686,531 A | 8/1987 | Shambroom et al. | 340/870.37 |
| 4,743,837 A | 5/1988 | Herzog | 324/60 |
| 4,763,063 A | 8/1988 | Shkedi | 324/60 CD |
| 4,814,691 A | 3/1989 | Garbini et al. | 324/61 R |
| 4,935,207 A | 6/1990 | Stanbro et al. | 422/68.1 |
| 4,958,129 A | 9/1990 | Poduje et al. | 324/661 |
| 5,028,876 A | 7/1991 | Cadwell | 324/678 |
| 5,325,442 A | 6/1994 | Knapp | 382/4 |
| 5,373,181 A | 12/1994 | Scheiter et al. | 257/415 |
| 5,430,381 A | 7/1995 | Dower | 324/452 |
| 5,467,022 A | 11/1995 | Aoki et al. | 324/661 |
| 5,493,621 A | 2/1996 | Matsumura | 382/125 |
| 5,530,581 A | 6/1996 | Cogan | 359/265 |
| 5,613,014 A | 3/1997 | Eshera et al. | 382/124 |
| 5,659,626 A | 8/1997 | Ort et al. | 382/125 |
| 5,767,686 A | 6/1998 | Kespohl | 324/662 |
| 5,778,089 A | 7/1998 | Borza | 382/124 |
| 5,825,907 A | 10/1998 | Russo | 382/124 |
| 5,828,773 A | 10/1998 | Setlak et al. | 382/126 |
| 5,841,888 A | 11/1998 | Setlak et al. | 382/124 |
| 5,844,415 A | 12/1998 | Gershenfeld et al. | 324/663 |
| 5,845,005 A | 12/1998 | Setlak et al. | 382/124 |
| 5,852,670 A | 12/1998 | Setlak et al. | 382/126 |
| 5,862,248 A | 1/1999 | Salatino et al. | 382/124 |
| 5,869,791 A | 2/1999 | Young | 178/20.01 |
| 5,903,225 A | 5/1999 | Schmitt et al. | 340/825.31 |
| 5,920,640 A | 7/1999 | Salatino et al. | 382/124 |
| 5,936,412 A | 8/1999 | Gershenfeld et al. | 324/663 |
| 5,953,441 A | 9/1999 | Setlak | 382/124 |
| 5,973,623 A | 10/1999 | Gupta et al. | 341/33 |
| 6,011,859 A | 1/2000 | Kalnitsky et al. | 382/124 |
| 6,025,726 A | 2/2000 | Gershenfeld et al. | 324/671 |
| 6,051,981 A | 4/2000 | Gershenfeld et al. | 324/663 |
| 6,066,954 A | 5/2000 | Gershenfeld et al. | 324/671 |
| 6,088,471 A | 7/2000 | Setlak et al. | 382/124 |
| 6,091,082 A | 7/2000 | Thomas et al. | 257/77 |
| 6,114,862 A | 9/2000 | Tartagni et al. | 324/662 |
| 6,191,593 B1 | 2/2001 | Tartagni et al. | 324/687 |
| 6,236,741 B1 | 5/2001 | Kovács-Vajna | 382/125 |

FOREIGN PATENT DOCUMENTS

| | | |
|---|---|---|
| EP | 0 454 883 B1 | 11/1991 |
| EP | 0 455 070 B1 | 11/1991 |
| EP | 0 710 593 A1 | 5/1996 |
| EP | 0 779 497 A2 | 6/1997 |
| EP | 0 779 497 A3 | 6/1997 |
| EP | 0 786 745 A2 | 7/1997 |
| EP | 0 786 745 A3 | 7/1997 |
| EP | 0 790 479 A1 | 8/1997 |
| EP | 0 791 899 A2 | 8/1997 |
| EP | 0 791 899 A3 | 8/1997 |
| GB | 2279756 A | 1/1995 |
| GB | 2279757 A | 1/1995 |
| GB | 2312514 A | 10/1997 |
| JP | 2000346608 A * | 12/2000 |
| WO | WO 97/40744 | 11/1997 |
| WO | WO 98/49691 | 11/1998 |
| WO | WO 99/28701 | 6/1999 |

OTHER PUBLICATIONS

Young et al., "Novel Fingerprint Scanning Arrays Using Polysilicon TFT's on Glass and Polymer Substrates," *IEEE Electron Device Letters,* 8(1):19–20, 1997.

Tartagni et al., "A 390dpi Live Fingerprint Imager Based on Feedback Capacitive Sensing Scheme," *IEEE International Solid–State Circuits Conference,* Feb. 7, 1997, 5 pp.

* cited by examiner

ENHANCED FINGERPRINT DETECTION

CROSS-REFERENCE TO RELATED APPLICATION

This application is a continuation-in-part of U.S. patent application Ser. No. 09/475,351 filed Dec. 30, 1999, now pending, which application is incorporated herein by reference in its entirety. Additionally, this application is related to U.S. patent application Ser. No. 09/475,686, filed Dec. 30, 1999 and currently pending.

TECHNICAL FIELD

This invention is related to fingerprint pattern recognition, and more particularly, to enhanced fingerprint pattern sensing circuit and method.

BACKGROUND OF THE INVENTION

Capacitive sensors to detect a fingerprint pattern are currently well known. There are a number of patents which describe capacitive sensors for determining the pattern of ridges and valleys in a person's fingerprint. U.S. Pat. No. 4,353,056 describes a capacitive fingerprint sensor which has a sensing surface for receiving a fingerprint and sensing the ridges and valleys of the skin using an array of small capacitors. U.S. Pat. No. 5,325,442 also describes a fingerprint sensing and recognition circuit using a plurality of capacitors arranged in rows and columns.

Some capacitive sensors operate using two or more plates in silicon with a negative feedback as shown in FIGS. 1 and 2, taken from U.S. Pat. No. 5,973,623. In the multiple plate system, the finger of the user changes the capacitance that exists between the two plates in silicon. A negative feedback circuit is used in the detection of whether a ridge or a valley is present in the fingerprint.

Some capacitive sensors operate using a single capacitor plate in silicon per sensor cell. This type of sensor is shown in U.S. Pat. No. 5,325,442. FIGS. 3 and 4 are prior art. Figures from this patent illustrate a single capacitive plate 14 and a switching device 16 to access the sensor cell. The finger of the user provides the other plate of the capacitor. The value of the capacitor is then sensed to determine the presence of a ridge or a valley.

One of the problems with the prior art capacitive fingerprint sensors is their level of sensitivity to distinguish a ridge from a valley. The difficulty of obtaining a good fingerprint pattern through capacitive sensing can vary from individual to individual. With some persons, depending upon their skin characteristics the pattern can be much more difficult to obtain than from other persons. It is therefore preferred to have an enhanced method of capacitive sensing which provides more uniform sensitivity from one individual to another.

SUMMARY OF THE INVENTION

According to principles of the present invention, a capacitive fingerprint sensing device is provided which places a variable voltage on the body of the individual whose fingerprint pattern is being sensed. The finger is thus performing the dual function of providing the variable charge transfer during input while also providing the variable capacitance to be sensed. The effect of performing both functions effectively multiplies the measurable effects of having a ridge or a valley at each sensor cell. The sensing is significantly enhanced in recognizing and distinguishing the difference between a ridge and a valley.

The electrical connection to the person's body can be made by any number of acceptable techniques. According to one preferred embodiment, an electrical contact is provided to the person's finger while it is placed on the fingerprint sensor pad. A logic control circuit connected to the electrical conductor places a step voltage on the electrical conductor according to a preset timing sequence in conjunction with the timing of the sensing. In this embodiment, there is a direct connection between the variable input voltage and the finger of the user for which the fingerprint is being sensed.

In a further embodiment, the voltage change is placed on the person's body by a capacitive transfer. A large plate capacitor in the silicon provides one plate to transfer charge to the finger to provide the change in voltage while the sensing occurs. Alternatively, the voltage change can be coupled to the body of the user either via another finger or some other appendage. For example, the connector can be in contact with the other hand of the person, their arm or any other acceptable portion of the body since all that is required is to place a change in charge on the person's body in order to obtain the enhanced capacitive sensing capability.

The invention can be used with sensor cells of the type having one capacitive plate in silicon and the finger providing the other plate, or with the type using multiple capacitor plates in silicon and the finger being a conductor that modifies their relative capacitance.

In one embodiment, the fingerprint or sensor circuit includes a negative feedback amplifier having the two plates of a feedback capacitor in silicon with a field therebetween. The field between the two plates is varied by the user's finger, whether ridge or valley. The effect of having a valley is that the sense capacitance will be greater than in the case of having a ridge. When a ridge is present, the feedback capacitance is reduced, as compared to a valley. In other words, the further the skin is from the plates of the capacitor, the less effect it has on reducing the effective capacitance between them and the sensed capacitance will be higher with a valley than with a ridge. On the other hand, the input capacitance will decrease with the greater distance of the skin from the sensor, such as is present at a valley. Since it is a ratio of the input capacitance to the sense (feedback) capacitance which determines the sensitivity of the circuit, a circuit which causes them to change in opposite directions results in a greatly multiplied effect of increasing the sensitivity of the measurement. Therefore, significant enhancement is provided by using the body as both the input capacitor and the variable plate to a capacitor whose value is being sensed.

DETAILED DESCRIPTION OF THE INVENTION

Figure 1:
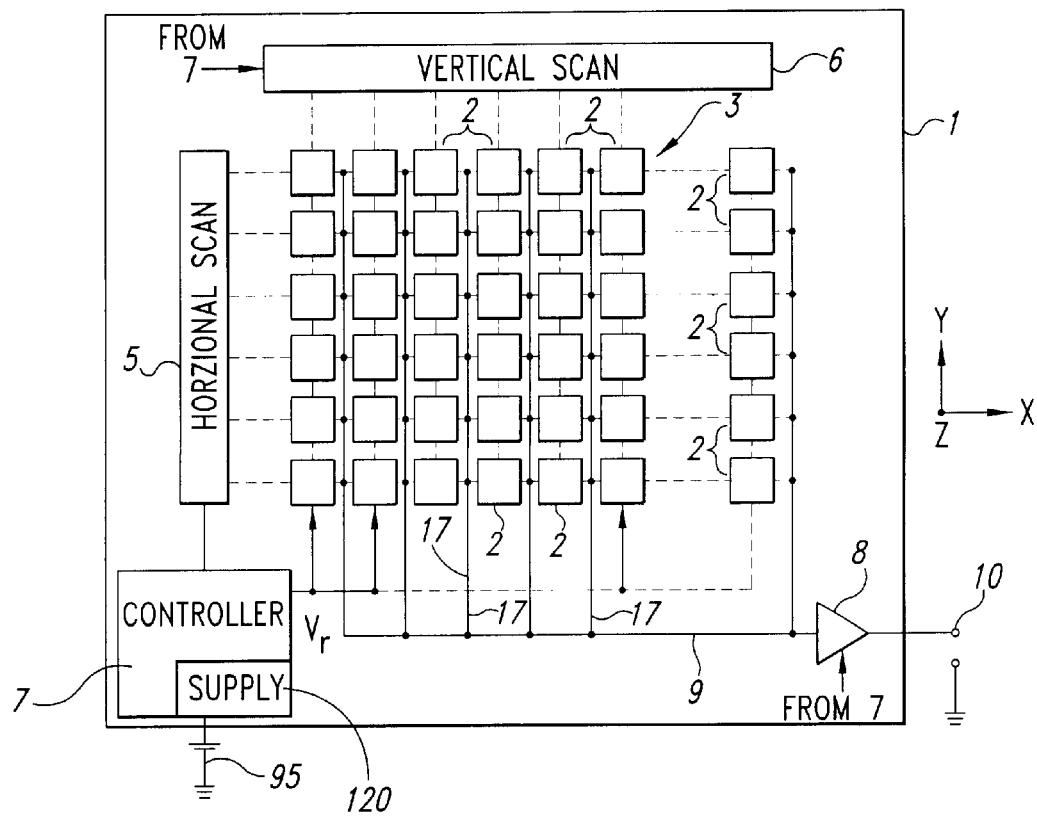
FIG. 1 is a schematic representation of a fingerprint sensor according to the prior art.

FIG. 1 illustrates a substrate 1 having a plurality of sensor cells 2 thereon. The sensor cells 2 are in the form of an array 3 and organized to sense a fingerprint pattern of a finger which is placed on top of the substrate. The array 3 is driven by horizontal scan electronics 5 and also by vertical scan electronics 6 so that each individual cell 2 is selected on a known timing sequence under control of the controller 7.

In particular, each sensor cell 2 includes electronics for sensing the presence or absence of a ridge or a valley of a fingerprint pattern for a finger which is placed on top of the substrate 1. The controller 7 includes a power supply circuit 120 which receives power from a power source 95. Each sensing cell 2 provides an output on line 17 of each individual column. The output is provided on the chip bus 9 which is provided to an output amplifier 8 and provided to the output of the sensor array 3 at terminal 10. The output of the sensor array 3 at terminal 10 is provided to fingerprint pattern recognition electronics which organizes the signal into a fingerprint pattern and compares it to other fingerprint patterns to perform recognition of the fingerprint pattern which is placed thereon. The specific details of the array 3 and interaction between the controller 7 to provide fingerprint pattern recognition is described in U.S. Pat. No. 5,973,623, which is incorporated herein by reference. The fingerprint pattern recognition may also be obtained and performed by any acceptable technique as described in many other patents and publications which are available to those of skill in the art today.

Figure 2:
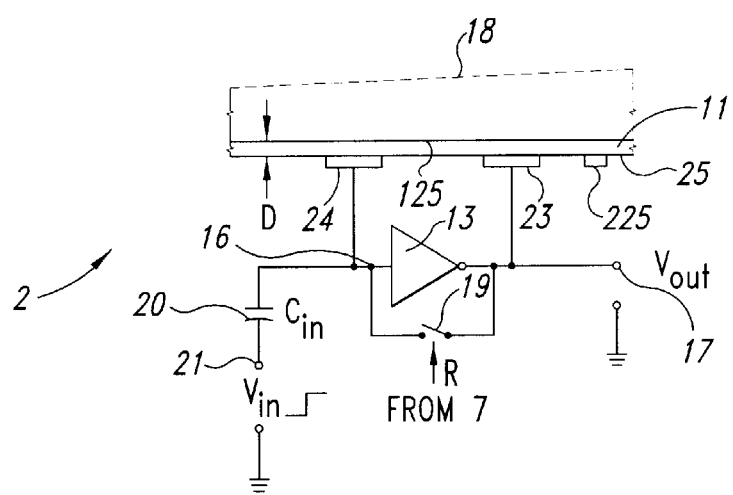
FIG. 2 is an electrical schematic representation of an individual cell of the fingerprint sensor of FIG. 1 according to the prior art.

FIG. 2 illustrates the electronics of a single sensor cell 2 which is acceptable for use in sensing the presence or absence of a ridge or valley according to the prior art. The cell shown in FIG. 2 is of the type that has two plates in the semiconductor substrate for each cell and the finger provides a third plate to modify the capacitance value of the existing capacitor. It can be considered a three plate cell, two plates in the substrate and one above. The specific electronics for the cell 2 are provided as only one example by which the cell can be constructed. Other acceptable techniques may also be used since the electronics of the individual cell are provided as an example only.

The cell 2 includes a dielectric layer 11 onto which a person's finger is placed. The dielectric layer 11 has a top surface 125 which comes in direct contact with the person's finger 18. The finger 18 will have a ridge or a valley at the position in which it comes in contact with the cell 2, the example shown for FIG. 2 including having a ridge thereon so that it is pressed against the substrate 11 and in contact with surface 125. The dielectric layer 11 has a thickness D as shown in FIG. 2.

A capacitor having plates 24 and 23 is against the back surface of the dielectric layer 11. The input plate of the cell 24 is connected to the input terminal of an inverting amplifier 13 and the output plate 23 is connected to the output of the inverting amplifier 13. A reset switch 19 is closed when sensing is not being performed to reset the inverting amplifier 13 to a known state. A capacitor 20 provides a step voltage N as applied through $V_{ref}$ at terminal 21. The capacitor $C_{in}$ is of a known value to provide a known charge to the input node 16 of inverting amplifier 13.

Figure 3:
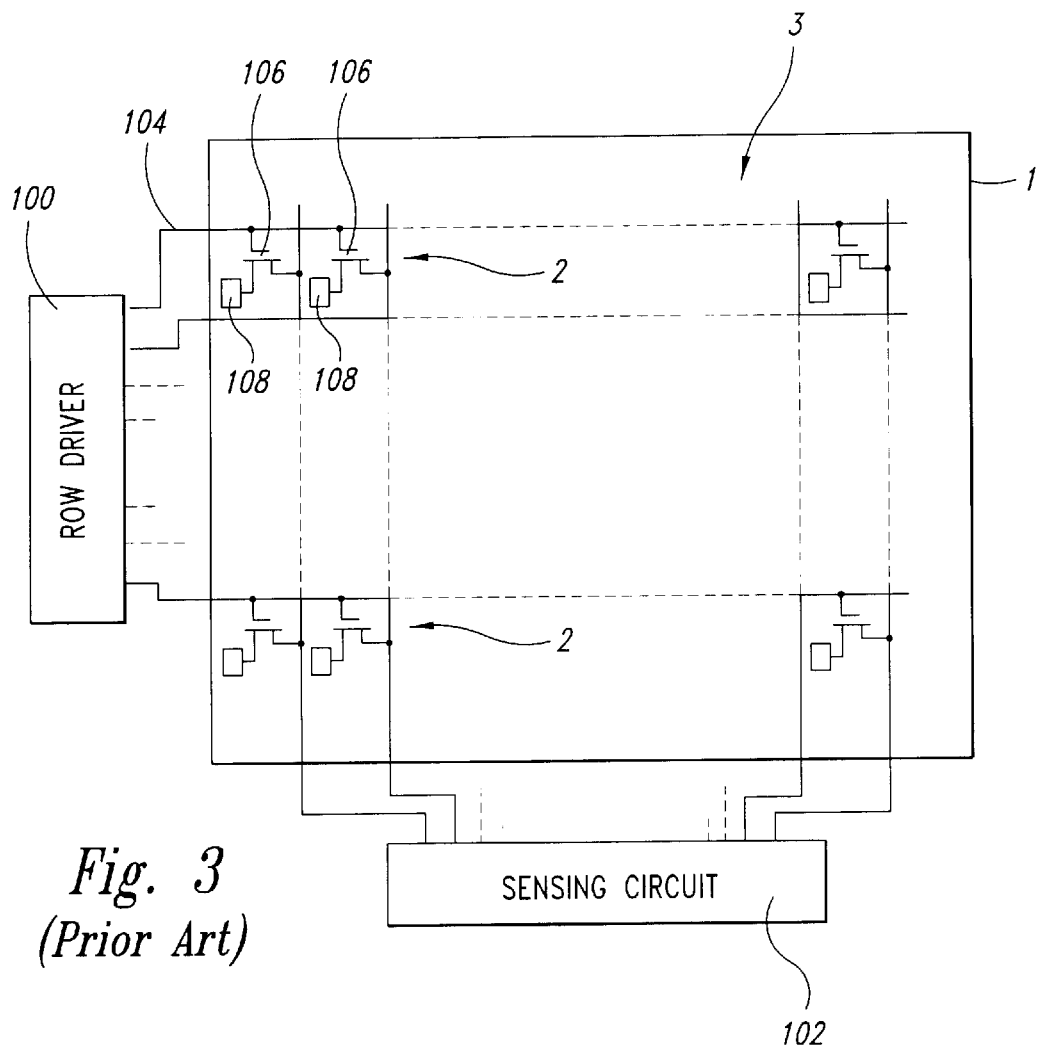
FIG. 3 is a schematic representation of a fingerprint sensor circuit according to different prior art embodiment.
Figure 4:
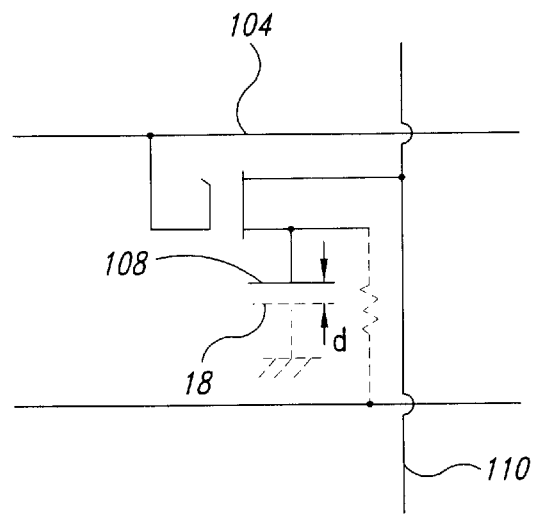
FIG. 4 is an electrical schematic of a fingerprint sensor cell as used in the prior art of FIG. 3.

FIGS. 3 and 4 illustrates another acceptable sensor array 3 and cell 2 which may be modified to use the present invention. The particular sensor cell 2 is known from prior art U.S. Pat. No. 5,325,442, to Knapp, which is hereby incorporated herein by reference. In particular, the sensor cell of the '442 patent to Knapp to include a row driver 100 and a sensor circuit 102.

The cell 2 of FIGS. 3 and 4 is of the type having one plate in the semiconductor substrate for each cell and the finger provides the second plate to form the capacitor with two plates. The row driver circuit couples to a row conductor 104 to the gate of an access transistor 106. One capacitor plate 108 in the substrate acts as a sense electrode. A finger 18 provides the other plate of the capacitor λ and the presence of a ridge or valley is determined based on the distance between the plate 108 and plate 18 that form the capacitor. The capacitance of the individual capacitors varies as a function of the spacing between the finger and the sense plate 108. The larger capacitance occurs where the finger ridge is adjacent and very close to the plate 108 and the smaller capacitances occurring where a valley is adjacent the plate 108, but spaced further from the plate because it is a valley.

The capacitive fingerprint sensor, whether the three plate cell of FIG. 2 or the two plate cell of FIG. 4, operates on the principle that the amount of charge stored on a capacitor is proportional to the voltage multiplied by the capacitance.

$$q=vc \tag{1}$$

where q equals the amount of charge, v equals the voltage on the capacitor, and C equals the capacitance value. As is known, the capacitance value of a capacitor varies with the distance of the plates from each other. In a fingerprint pattern sensor, the fingerprint, whether a ridge or a valley, acts as a plate of the capacitor. The distance varies in the fingerprint, small for a ridge and large for a valley, the capacitance is also different. In a three plate sensor, such as FIG. 2 shows, the capacitance value also varies depending upon the fringing effect between the two capacitor plates in the substrate as described by the later equations herein.

The value of the charge stored or the rate of charge stored can be measured and sensed in one embodiment, if desired. This is done in some devices by placing a current or voltage on the capacitor and obtaining a measurement corresponding to the stored charge.

A variation on this method is to measure a change in output voltage based on a change of charge on the capacitor. The basic equation for output voltage sensing can be obtained from equation 1 as follows:

$$V_{out} = \frac{q}{C} \quad (2)$$

where $V_{out}$ is the output voltage from the cell 2 and q is the charge, and C is the capacitive value.

It is often desirable to measure a change in $V_{out}$ from a known reset of reference value rather than measure $V_{out}$ as an absolute value. For cells in which a change in voltage is measured to sense a ridge or a valley, the following equation applies:

$$\Delta V_{out} = \frac{\Delta q}{C_s} \quad (3)$$

in which $\Delta V_{out}$ equals the change in voltage on terminal 17, $\Delta q$ equals the change in charge on the capacitance, and $C_s$ is the capacitance being sensed, namely, the capacitance of the capacitor plates in the sensor with the finger 18 adjacent thereto, whether a ridge or a valley. The presence of a ridge and a valley will cause a variation in the changes in the capacitance. In particular, as described later herein, the presence of a ridge or a valley near sensor cell 2 will cause the capacitance being sensed to be reduced or increased, respectively, so that a ridge and a valley can be distinguished.

Figure 5:
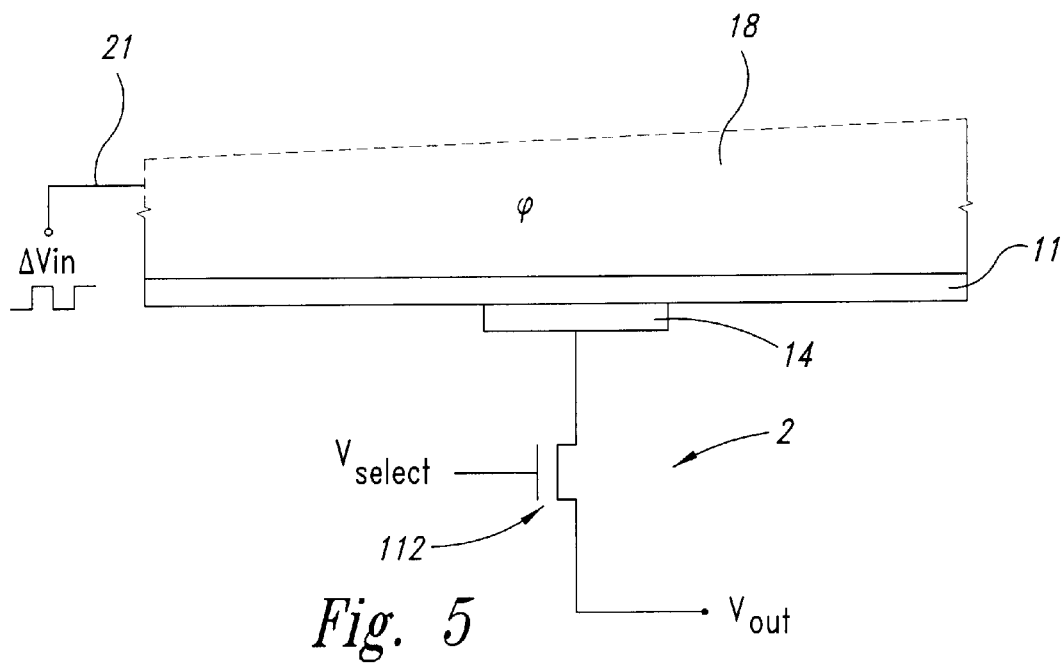
FIG. 5 is an electrical schematic of a fingerprint sensor according to principles of the present invention.
Figure 6:
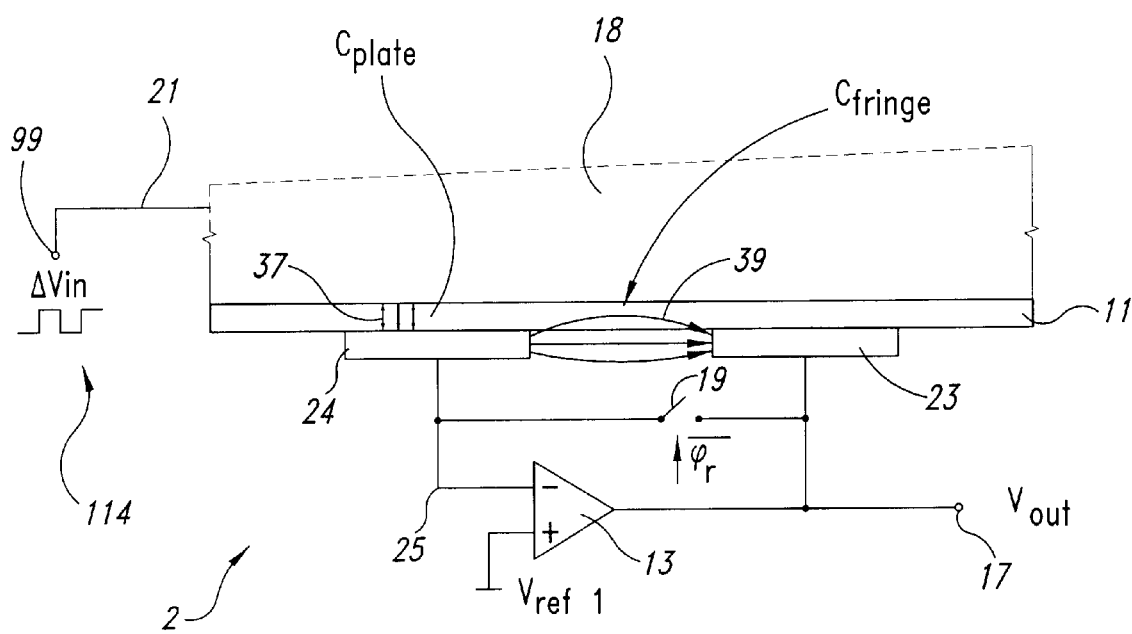
FIG. 6 is a schematic representation of a fingerprint sensor according to principles of the present invention.
Figure 7:
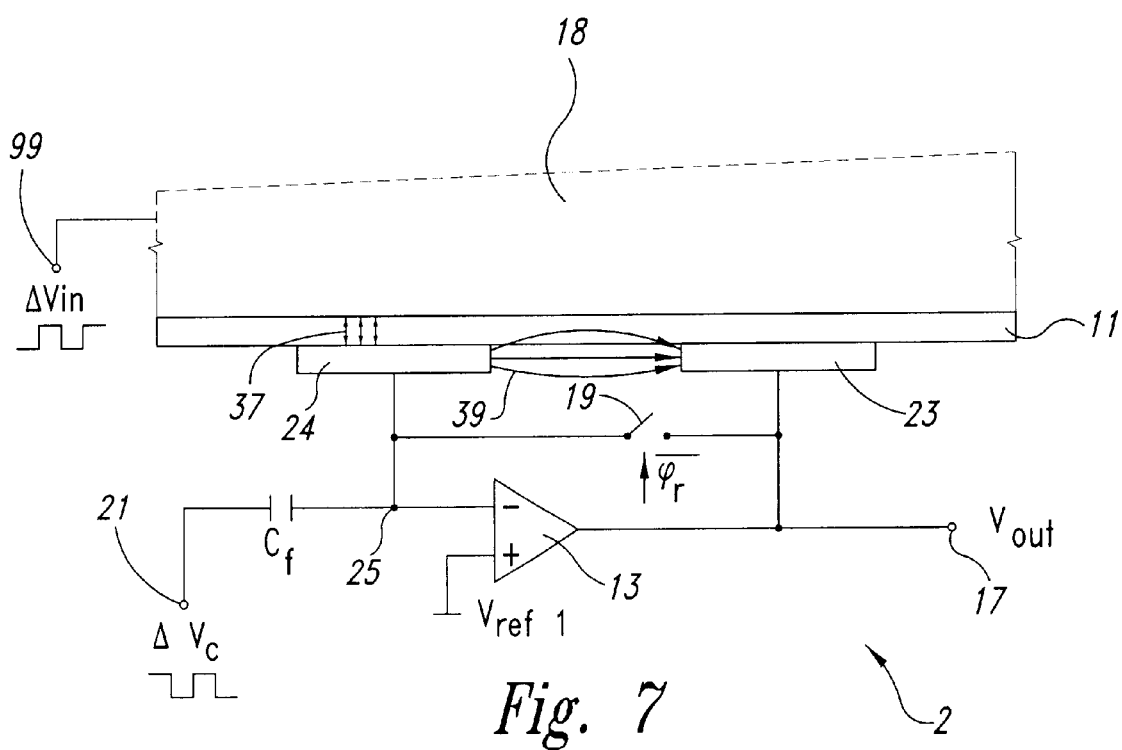
FIG. 7 is an electrical schematic of an alternative embodiment of a fingerprint sensor according to principles of the present invention.

FIGS. 5, 6 and 7 illustrate, respectively, alternate embodiments according to the present invention. In each of the FIGS. 5–7, a dielectric layer 11 is positioned over a sensor cell 2. Directly on top of the dielectric layer 11, a finger 18 of a user is positioned for sensing the fingerprint pattern. Of course, the term fingerprint as used herein includes the variations in skin texture on any body part of a person, such as a thumb, a toe, a foot, a forehead, or any other surface whose variations are being sensed to identify a person. In the examples shown in FIGS. 5–7, the finger 18 has a ridge directly over the sensor cell 2. Accordingly, the finger appears as a single flat member against the substrate 11. Since, in most cases, a sensor cell 2 will be smaller than the width of a ridge it will appear, from the view of the cell 2, that the finger 18 is abutting against the top surface of the dielectric layer 11. In other figures, such as FIGS. 8A, 8B, 9, 15A and 15B, a plurality of different sensor cells 2 are shown to illustrate the response of the array to different parts of the fingerprint, whether a ridge or a valley.

The operation of the circuit of FIG. 5 is illustrated schematically in FIGS. 8A and 8B, as will now be explained. The circuit of FIGS. 6 and 7 is illustrated schematically in FIGS. 9 and 10 and they will be discussed in more detail with respect to these two figures.

Figure 8A:
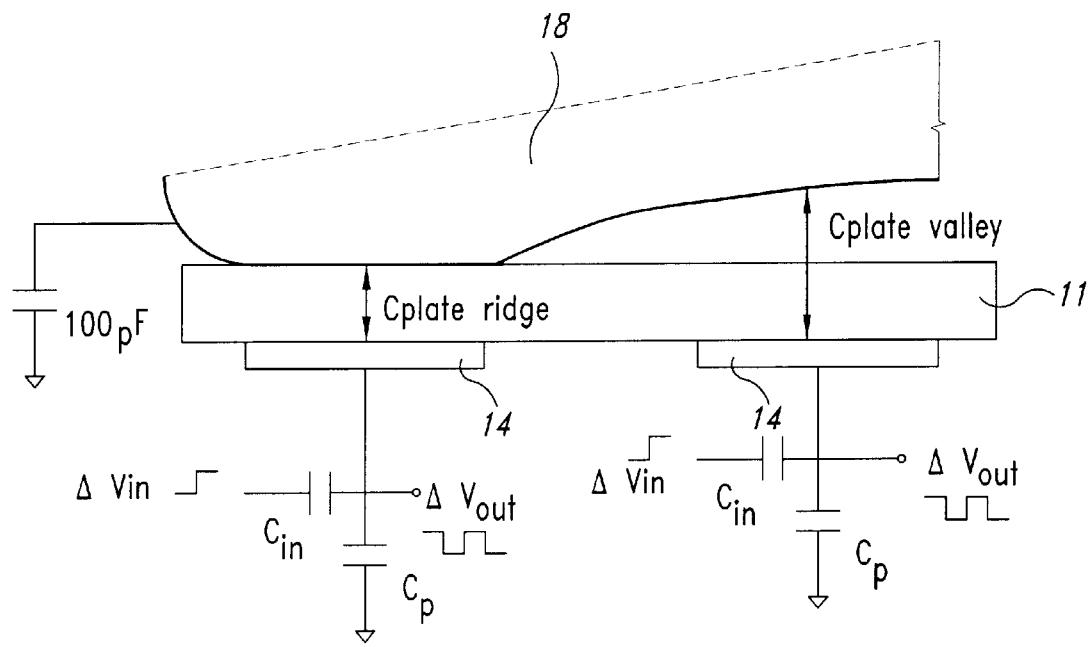
FIG. 8A is an electrical schematic of fingerprint sensor cells for aid in understanding the present invention.
Figure 8B:
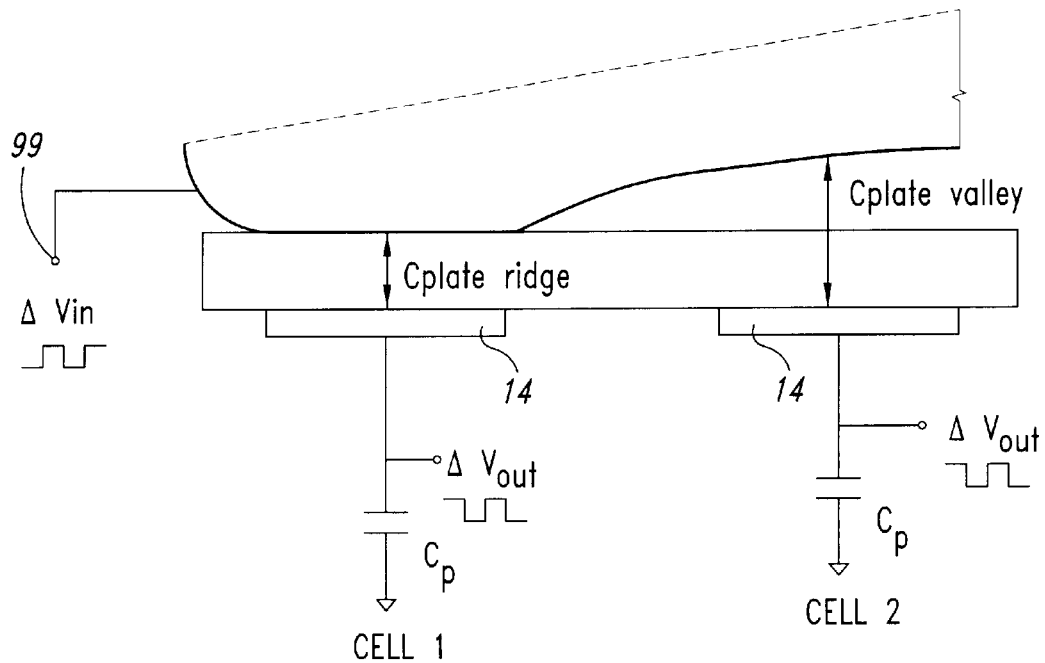
FIG. 8B is an electrical schematic of fingerprint sensor cells illustrating one embodiment of the invention.

FIGS. 8A and 8B illustrate the sensing principles to illustrate the present invention using a sensor cell of the type generally shown in FIG. 5. FIG. 8A shows a two plate capacitor system for each cell, the finger 18 being one plate and the plate 14 being the sensor electrode and other plate. Two cells are shown, one at a ridge and the other at a valley.

While in the ideal case, $C_s$ is the only capacitance which effects the equation such that equation (3) is a direct characterization solely of the finger being sensed output, in reality, there are various parasitic capacitance which occur in different parts of the circuit. If the effect of all the parasitic capacitance at the various parts of the circuit are combined, they are summed with the capacitance being sensed as shown by equation (4) below:

$$\Delta V_{out} = \frac{\Delta q}{C_s + C_p} \quad (4)$$

where $C_p$ is the parasitic capacitance affecting the cell output. Unfortunately, the parasitic capacitance $C_p$ can sometimes be quite large. Depending on the particular circuit design $C_p$ may be much larger than $C_s$. In some cases it may be over ten times larger. If $C_p$ is too large, then it will dominate the equation such that changes in $C_s$ cause only a very small change in the overall capacitance being sensed as can be seen by viewing equations (2) and (4) together. Accordingly, if the parasitic capacitance is much, much larger than the capacitance being sensed, then the sensitivity of cell 2 is reduced. In most applications, the capacitance being sensed is extremely small since it is based on detecting merely the difference in capacitance value between a ridge and a valley in a single fingerprint.

The sensitivity of the sensor can be defined based on the ability to distinguish between the maximum signal output and the minimum signal output. As an equation, sensitivity can be expressed as $$\delta = \frac{\Delta V_{out\ max} - \Delta V_{out\ min}}{\Delta V_{out\ min}} \quad (5)$$

where $\delta$ is the sensitivity, $\Delta V_{outmax}$ is the highest possible output voltage and $\Delta V_{outmin}$ is the lowest possible output voltage during a measurement. The sensitivity thus increases with a larger difference between the maximum and minimum changes in output voltages and by reducing the minimum change in output voltage to the lowest possible value.

In the circuit of FIG. 8A, the output voltage will be different from cell 1 to cell 2 based on the difference between $C_{plate\ ridge}$ and $C_{plate\ valley}$. All other aspects of the cells will be the same. Thus, both cells will have the same $C_{in}$ value and the same $C_p$ value.

Viewing now FIG. 8A, the change in output voltage can be defined by:

$$\Delta V_{out} = \frac{\Delta V_{in} \cdot C_{in}}{C_{in} + C_p + C_{plate\ body}} \quad (6)$$

where $\Delta V_{in}$ is the change in input voltage during sensing, $C_{in}$ is the input capacitor, $C_p$ is the parasitic capacitor and $C_{plate\ body}$ is the capacitance that is composed of the plate 14 and the body 18.

It is, of course, desired to distinguish for the body, $C_{plate\ body}$, the difference between a ridge and a valley, defined as $C_{plate\ ridge}$ and $C_{plate\ valley}$, respectively.

The plate capacitor value is at its maximum for a ridge and its minimum for a valley, so equation (6) becomes:

$$\Delta V_{out\ max} = \frac{\Delta V_{in} \cdot C_{in}}{C_{in} + C_p + C_{plate\ valley}} \quad (7)$$

for a valley over the cell, as shown for cell 2. For a ridge, the results are:

$$\Delta V_{out\ min} = \frac{\Delta V_{in} \cdot C_{in}}{C_{in} + C_p + C_{plate\ ridge}}. \quad (8)$$

Since $C_{plate\ ridge}$ is larger than $C_{plate\ valley}$ by some factor $\Delta$, these equations can be simplified by stating that:

$$C_{plate\ ridge} = C_{plate\ valley} + \Delta C_{plate\ ridge} \quad (9)$$

where $\Delta C_{plate\ ridge}$ is the difference in capacitance between a valley and a ridge. Substituting this into equation (9) provides:

$$\Delta V_{out\ min} = \frac{\Delta V_{in} \cdot C_{in}}{C_{in} + C_p + C_{plate\ ridge} + \Delta C_{plate\ ridge}}. \quad (10)$$

It is desired to understand the overall sensitivity of the system, which was stated in equation (5) and is provided again below.

$$\delta = \frac{\Delta V_{out\ max} - \Delta V_{out\ min}}{\Delta V_{out\ min}}. \quad (11)$$

Substituting equation (7) and (10) for the above values, equation (12) is obtained:

$$\delta = \frac{\Delta C_{plate\ ridge}}{C_{in} + C_p + \Delta C_{plate\ valley}}. \quad (12)$$

It can be seen that the effect of both parasitic capacitance $C_p$ and input capacitance $C_{in}$ is to reduce effective sensitivity. We can define idealized sensitivity for the plate, $\delta_{plate}$, (in the absence of parasitics) to be:

$$\delta_{plate} = \frac{\Delta C_{plate\ ridge}}{C_{plate\ valley}}. \quad (13)$$

For simplicity from an algebra standpoint, a value $\alpha$ will be set equal to $$\alpha = \frac{C_{in} + C_p}{C_{plate\ valley}}. \quad (14)$$

If equations (13) and (14) are substituted into equation (12). The result is:

$$\delta = \frac{\Delta C_{plate\ ridge}}{C_{plate\ valley}} \cdot \frac{1}{1+\alpha} = \delta_{plate} \cdot \frac{1}{1+\alpha}. \quad (15)$$

In a semiconductor substrate, $C_{in}$ can be carefully controlled and can be reduced to a very low value so as to be negligible, approaching zero. On the other hand, $C_p$ will be over 10 times greater than $C_{plate\ valley}$, may be up to 20 to 100 times greater. $C_p$ is difficult to reduce to zero, so we assume $C_p$ equals $10 \times C_{plate\ valley}$.

This provides $$\alpha = \frac{0+10}{1} = 10 \quad (16)$$

and so resulting effective sensitivity is:

$$\delta = \frac{\delta_{plate}}{11}. \quad (17)$$

Thus, for this type of sensing, the sensitivity is reduced to the plate sensitivity $\delta_{plate}$, divided by 11. The effect of $C_p$ thus causes a significant reduction in sensitivity. As $C_p$ becomes higher, the sensitivity will reduce even further.

FIG. 8B illustrates one embodiment of the present invention showing how applying $V_{in}$ to the body can increase the sensitivity and reduce the effects of $C_p$. In FIG. 8B, the step voltage $\Delta V_{in}$ is applied to the finger 18 and the body acts as capacitor $C_{in}$. In this case, the value of $C_{in}$ will be different for each cell, depending on whether a valley or a ridge is present over the cell. For cell 1, a ridge, the value $C_{in}$ will be higher for a ridge and lower for a valley. The capacitance change caused by ridge or valley being present can be effectively considered as multiplying the change in output since it affects both the input signal and the sense signal. The results can be seen from the following equations:

$$\Delta V_{out} = \frac{C_{plate\ body} \cdot \Delta V_{in}}{C_{plate\ body} + C_p}. \quad (18)$$

Recalling that $C_{plate\ ridge}$ is larger than $C_{plate\ valley}$ by a value $\Delta C_{plate\ ridge}$ and that $\delta_{plate}$ is defined as $$\frac{\Delta C_{plate\ ridge}}{C_{plate\ valley}},$$

the following equations are obtained:

$$\Delta V_{out\ max} = \frac{\Delta V_{in}(C_{plate\ valley} + \Delta C_{plate\ ridge})}{C_{plate\ valley} + \Delta C_{plate\ ridge} + C_p} \quad (19)$$

$$\Delta V_{out\ min} = \frac{\Delta V_{in}(C_{plate\ valley})}{C_{plate\ valley} + C_p} \quad (20)$$

$$\delta = \frac{\Delta V_{vout\ max} - \Delta V_{vout\ min}}{\Delta V_{vout\ min}} = \frac{\Delta C_{plate\ ridge}}{C_{plate\ valley}} \cdot \frac{C_p}{C_{plate\ valley} + \Delta C_{plate\ ridge} + C_p}. \quad (21)$$

Equation (21) shows that $C_p$ is in both the numerator and denominator. Thus the effect of $C_p$ will be to cancel itself out, towards a value equal to 1 in the equation. Even if $C_p$ becomes large, the result will be to cancel out its effect on the sensitivity since it is in both top and bottom in the ratio. Defining $$\beta = \frac{C_{plate\ valley} + \Delta C_{plate\ ridge}}{C_p} \quad (22)$$

for algebraic simplicity, we get $$\delta = \frac{\Delta C_{plate\ ridge}}{C_{plate\ valley}} \left( \frac{C_p}{C_{plate} + \Delta C_{plate\ ridge} + C_p} \right) = \delta_{plate} \cdot \frac{1}{1+\beta}. \quad (23)$$

Thus, if we assume again that $C_p = 10 C_{plate\ valley}$, along with the further assumption that $C_p \approx \Delta C_{plate\ ridge}$, the results obtained from the above equations show that $$\frac{1}{1+\beta} \approx \frac{1}{2} \quad (24)$$

so that:

$$\delta = \frac{\delta_{plate}}{2}. \quad (25)$$

Equation (25) shows that the invention results in a 5-times improvement in sensitivity for the invention applied to the simple case of FIG. 8B.

FIG. 5 shows a circuit of a single cell that takes advantage of the principles of the invention that have just been shown in the example of FIG. 8B. A select transistor 112, coupled to a plate 14 having a finger 18 thereon provides an output $V_{out}$. A voltage terminal 21 having a step voltage input signal $V_{in}$ is connected to the finger 18.

FIG. 6 illustrates another example of fingerprint sensing according to principles of the present invention. The sensor cell as shown in FIG. 6 is a further example that provides even more remarkable results than the single plate sensor cell of FIG. 5 as explained herein as will be clear from the technical discussion.

According to principles of the present invention, during the sensing operation, an electrical conductor 21 is connected to the body of the person whose fingerprint is being sensed. It may be coupled at any convenient location, such as the finger itself whose print is being sensed, the hand of the user, the unused hand of the user, the foot, via a conductive foot pad, or other location. Electrical conductor 21 has a terminal 99 connected to a variable voltage supply $\Delta V_{in}$. The $\Delta V_{in}$ is directly controlled in a timing sequence with electronic controller 7 to place a known change of voltage on the body and thus on the finger 18 in conjunction with the timing of sensing in each individual cell 2. In particular, at the beginning of sensing, the $\Delta V_{in}$ will normally be a low value and, once sensing has begun will undergo step voltage to high value as shown by the signal wave 114 applied to the terminal $\Delta V_{in}$. After the sensing has occurred while the voltage $\Delta V_{in}$ is at a high value then the cell 2 will be reset and the electrical conductor 21 will be returned to a low value so as to place the both the cell and the body in a reset mode in preparation for the next sensing cycle at which time $\Delta V_{in}$ undergoes another step value upwards as shown by signal wave 114 in FIG. 4.

The step on $\Delta V_{in}$ is timed in conjunction with the timing sequence of a clock signal $\phi_r$ which controls the opening and closing of switch 19. Namely, switch 19 is opened and after which the $\Delta V_{in}$ undergoes the step function upwards so that the change in voltage $\Delta V_{in}$ occurs when switch 19 is open. This creates a change on input node 25 to inverting amplifier 13 which creates a change in voltage on $V_{out}$ corresponding to $\Delta V_{out}$ as discussed in the prior equations.

The three plate capacitor system of FIGS. 2, 6, 7, 9, and 10 causes a change in the output voltage by two effects, the plate effect, already discussed, and the fringing effect between the two plates 23 and 24. For the fringing effect, the presence of a ridge will greatly reduce the fringe capacitive between plates 23 and 24, whereas a valley will cause little or no reduction. Having a conductor adjacent the plates of the capacitor will ground some of the field lines between the capacitance plates. On the other hand, if a valley is present over sensor cell 2, then the sensed capacitance Cs will be greater than that of a ridge since a valley has a conductor spaced farther from the cell 2. In the ideal sense, the reduction of capacitance may be zero though, in a real sense, even a valley may cause some slight reduction in the capacitance value. Nevertheless, the general principle applies for a multiple plate capacitive sensor that Cs will be larger with a greater distance of the finger 18 from the cell such as occurs at a valley and Cs will decrease with the finger closer to the cell such as occurs at a ridge. Namely, the sensed plate capacitance Cs for a valley is greater than for a ridge.

Comparing the plate effect and the fringe effect provides:

$$C_{plate\ ridge} > C_{plate\ valley} \quad (26)$$

$$C_{fringe\ ridge} < C_{fringe\ valley}. \quad (27)$$

As previously stated, $$C_{plate\ ridge} = C_{plate\ valley} + \Delta C_{plate\ ridge} \quad (9)$$

and $$\delta_{plate} = \frac{\Delta C_{plate\ ridge}}{C_{plate\ valley}}. \quad (13)$$

For the fringe capacitance, between plates 23 and 24, it can also be stated that:

$$C_{fringe\ valley} = C_{fringe\ ridge} + \Delta C_{fringe\ valley} \quad (28)$$

and that:

$$\delta_{fringe} = \frac{\Delta C_{fringe\ valley}}{C_{fringe\ ridge}} \quad (29)$$

where $\delta_{fringe}$ is the idealized sensitivity between plates 23 and 24 for the fringe capacitor.

Viewing FIG. 2, the prior art results of the sensing with $V_{in}$ applied to the capacitor $C_{in}$ can be seen in the equations:

$$-\Delta V_{out} = \frac{\Delta V_{in} \cdot C_{in}}{C_{fringe\ body}} \quad (30)$$

$$-\Delta V_{out\ max} = \frac{\Delta V_{in} \cdot C_{in}}{C_{fringe\ ridge}} \quad (31)$$

$$-\Delta V_{out\ min} = \frac{\Delta V_{in} \cdot C_{in}}{C_{fringe\ ridge} + \Delta C_{fringe\ valley}}. \quad (32)$$

When these equations are put into the sensitivity equation, (11), the result is:

$$\delta = \frac{\Delta V_{out\ max} - \Delta V_{out\ min}}{\Delta V_{out\ min}} = \frac{\Delta C_{fringe\ valley}}{C_{fringe\ ridge}}. \quad (33)$$

Turning now to FIG. 6, in which the invention is used to apply the input voltage to the body. The fringe capacitor, $C_{fringe}$ is represented by field lines 39 and $C_{plate}$ by field lines 37, the results obtained will be:

$$-\Delta V_{out} = \frac{\Delta V_{in} \cdot C_{platebody}}{C_{fringebody}} \quad (34)$$

recalling the equations for $C_{fringe\ ridge}$ and $C_{fringe\ valley}$, the following is obtained:

$$-\Delta V_{out\ max} = \frac{\Delta V_{in}(C_{plate\ valley} + \Delta C_{plate\ ridge})}{C_{fringe\ ridge}} \quad (35)$$

$$-\Delta V_{out\ min} = \frac{\Delta V_{in}(C_{plate\ valley})}{C_{fringe\ ridge} + \Delta C_{fringe\ valley}} \quad (36)$$

$$\delta = \frac{\Delta V_{out\ max} - \Delta V_{out\ min}}{\Delta V_{out\ min}} \quad (37)$$

$$\delta = \frac{\Delta C_{fringe\ valley}}{C_{fringe\ ridge}} + \frac{\Delta C_{plate\ ridge}}{C_{plate\ valley}} + \frac{\Delta C_{fringe\ valley} \cdot \Delta C_{plate\ ridge}}{C_{fringe\ ridge} \cdot C_{plate\ valley}} \quad (38)$$

$$\delta = \delta_{fringe} + \delta_{plate} + \delta_{fringe} \cdot \delta_{plate}. \quad (39)$$

As can be seen, the idealized sensitivity increases greatly over the prior art.

Figure 9:
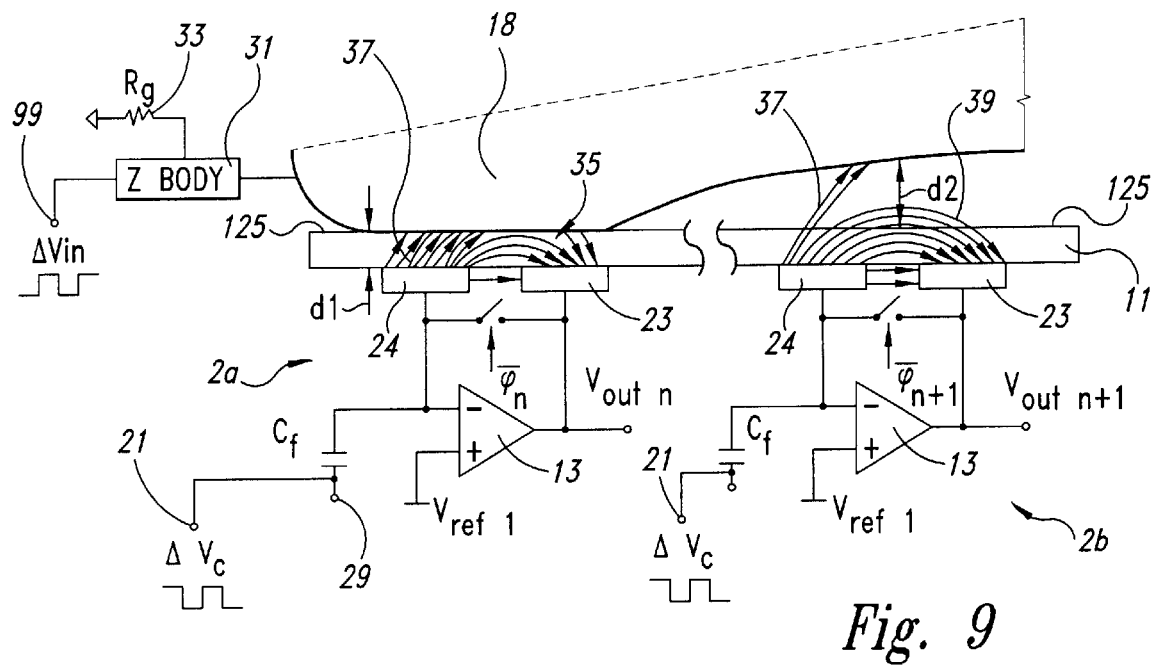
FIG. 9 is an electrical schematic of a plurality of cells while sensing a fingerprint ridge and valley pattern according to an embodiment of the present invention.
Figure 10:
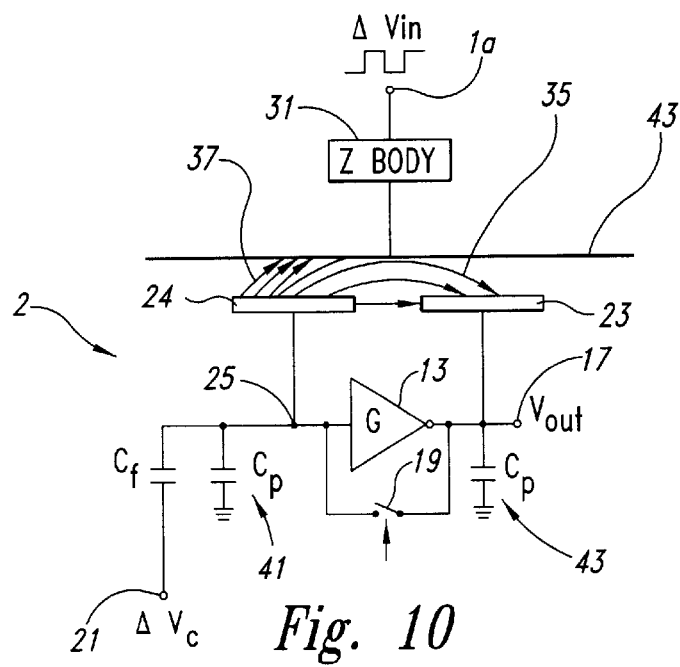
FIG. 10 is an electrical equivalent circuit showing the electrical interaction between various equivalent electrical components according to principles of the present invention.

Turning now to FIGS. 7, 9 and 10. A further embodiment of a circuit is shown in FIG. 7, and theoretical schematics are shown in FIGS. 9 and 10. In this embodiment, an additional compensation voltage $\Delta V_c$ is applied to a filter capacitor $C_f$ with the voltage $\Delta V_c$ being opposite the wave form $\Delta V_{in}$.

In the non-ideal case, the grain G of amplifier 13 is finite and, as shown in FIG. 10, there are parasite capacitors $C_p$ on the input and output nodes to the amplifier 13.

Since the body is being used as the input capacitor, the value of the $C_{plate}$ contribute to the total input node capacitance.

$$\Delta V_{out} = \frac{\Delta V_{in} \cdot C_{plate\ body}}{\frac{G+1}{G}C_{fringebody} + \frac{C_{platebody} + C_p}{G}} \quad (40)$$

for a very, very large G, one of the factors goes to 1 and the other factor goes to zero so:

$$\Delta V_{out} = \frac{\Delta V_{in} \cdot C_{platebody}}{C_{fringebody}}. \quad (41)$$

Substituting from prior equations provides $$\delta = \frac{\delta_{plate}}{1+\sigma} + \frac{\delta_{plate} \cdot \delta_{fringe}}{1+\varepsilon} + \frac{\delta_{fringe}}{1+\varepsilon}. \quad (42)$$

As G becomes large then $\sigma$ goes toward zero and $\varepsilon$ goes toward zero.

The invention thus has the affect, in the non-ideal case of canceling out completely the parasitic capacitance as well as increasing the sensitivity as the gain G of amplifier 13 goes higher. In the above equation (42), $$\sigma = \frac{C_{plate\ valley} + C_{plate\ ridge}}{(G+1)C_{fringe\ ridge} + C_p} \quad (43)$$

and $$\varepsilon = \frac{C_{plate\ valley} + \Delta C_{plate\ ridge} + C_p}{(G+1)C_{fringe\ ridge}}. \quad (44)$$

The result obtained, even in the non-ideal case with a large, but finite gain G, thus approaches:

$$\delta = \delta_{plate} + \delta_{plate} \cdot \delta_{fringe} + \delta_{fringe}. \quad (45)$$

FIG. 7 illustrates an alternative embodiment for a circuit according to principles of the present invention. Now that the mathematical calculations have been shown, the circuit of FIG. 7 will be described in more detail. Namely, the circuit of FIG. 7 is different from FIG. 6 in that a separate capacitor $C_f$ is present on the input 25. This separate capacitor $C_f$ acts as a compensation capacitor or filter to the input node 25 to enhance and further increase the sensitivity. One plate of the capacitor $C_f$ is connected to the sense node 25 whereas the other plate of the capacitor is connected to a voltage source $V_c$ representing a compensation voltage. The voltage source $V_c$ also undergoes a change in voltage according to a known timing sequence and thus is shown as a $\Delta V_c$. In a preferred embodiment, the compensation voltage $\Delta V_c$ undergoes a change in voltage which is exactly opposite that of $\Delta V_{in}$ which is placed on the body. Namely, the signals $\Delta V_{in}$ and $\Delta V_c$ will normally be the inverse of each other such that when $\Delta V_{in}$ undergoes a step function up, $\Delta V_c$ will undergo step down. According to principles of the present invention, the magnitude and absolute direction of $\Delta V_{in}$ and $\Delta V_c$ is not critical; a change in voltage of some magnitude is desired. Namely, the $\Delta V_{in}$ shown in FIG. 7 as undergoing a step function from a low signal to a high signal could, of course, undergo a change from a low signal to a negative voltage, or from a high signal to a low signal to place the change in voltage on the finger 18. Similarly, $\Delta V_{in}$ can transition from low to high and from high to low, respectively, as shown in FIG. 7 or can transition from high to low and from low to high, respectively, in order to provide the enhanced sensing according to principles of the present invention.

FIGS. 9 and 10 will be used to illustrate the theory of the operation. As will be appreciated, the mathematical equations which characterize the human body, and the electrical interaction between the human body and the sensor cell are very complicated if all factors and parasitics are included therein. Accordingly, not all possible factors and parasitics are shown and a simplified electrical explanation is provided that includes the major factors so that the basic operation of the invention can be understood.

As shown in FIG. 9, the terminal 99 has applied thereto a change in voltage $\Delta V_{in}$ and the terminal 29 also as applied thereto, a change in voltage $\Delta V_c$ as previously described with respect to FIG. 7. Viewing now the connection between the $\Delta V_{in}$ at terminal 99 and the actual finger 18, it can be seen that the human body has a certain impedance shown as Z BODY 31. The impedance of the body 31 is characterized according to a number of different electrical equations, and is sufficient for purposes of the invention to view the overall impedance of the body whether composed of various capacitors, resistors or combinations thereof as the overall body impedance 31. The body also has a resistance to ground 33 which varies greatly from one person to another and also varies based on the position of connection to the body. As can be appreciated, in some embodiments the resistance to ground 33 characterized by resistor $R_g$ can be extremely large.

For example, if the person is electrically insulated from ground, such as having thick rubber soles, then the resistance $R_g$ will approach infinity so that in fact, the person is not grounded and, from an electrical voltage potential, the voltage on the body is floating. In other embodiments, the resistance $R_g$ will be extremely small, because the body is connected directly to ground. For example, if the human skin is in direct electrical contact with the grounding electrode, then resistance to ground 33 will be very small. Accordingly, the value for resistor $R_g$ may vary from one circumstance to another.

FIG. 9 shows two sensor cells 2 which are spaced from each other in different parts of array 3. For ease of illustration, the first cell 2 is shown with a ridge directly over the cell 2, whereas the second cell is shown with a valley over the cell 2 so that the differences in operation can be easily explained and understood. Concerning first the situation in which a ridge of the finger 18 is directly over the cell 2. In this situation, the distance between the skin is $D_1$ since the skin is in direct contact with the upper surface 125 of the dielectric layer 11. In this instance, the effect of the ridge 18 is to reduce the value of the fringe capacitance between plates 24 and 23 of the negative feedback amplifier 13. In particular, the capacitance between plates 24 and 23 is shown by the fringe field lines 35 with fewer field lines illustrated in a reduction in the capacitance value. Namely, since the ridge 18 is close to the plates 24 and 23, some of the field lines are interfered with by the finger 18 so that the overall capacitance value between 24 and 23 is reduced due to the fringing effect of an adjacent conductor. This is represented by some of the field lines 35 going into the finger 18 rather than extending between capacitor plate 24 and 23.

The input capacitance, which is an active part of the sensing circuit, also has effect on the sensor cell 2. Namely, the input capacitor $C_{in}$ is also variable as coming from the body will go high at a ridge, as compared to a valley. Namely, $C_{in}$ has its maximum value at a ridge. $C_s$, on the other hand, goes down at a ridge, namely $C_s$ will have its minimum value at a ridge. The recognition that a ridge has an opposite effect on the two capacitance values, namely that it causes a decrease in the fringe capacitance $C_s$, which is sensed and an increase in the input capacitance is a principle of the present invention, which is used to provide enhanced sensitivity for fingerprint pattern recognition.

According to the mathematical equations for sensing the fingerprint pattern, $C_{in}$ and $C_s$ are a ratio which is used for changing the output value $V_{out}$. Thus, if $C_s$ and $C_{in}$ change in opposite directions, this will have the effect of greatly changing the ratio, particularly, over the change that would occur if only one of the values $C_s$ or $C_{in}$ were to change. In particular, according to principles of the present invention, the body itself is used as the input capacitor as well as for the sense capacitor so that enhanced sensitivity is obtained, as will be explained with respect to the following equations. For understanding the charge change which takes place on the body when the voltage step $\Delta V_{in}$ is applied thereto, it can be appreciated that:

$$Q_{in}=\Delta V_{in}(C_{in}) \tag{46}$$

where $Q_{in}$ is the amount of charge which is placed on the body, and thus corresponds to $\Delta_q$ when the body undergoes a change in voltage. $\Delta V_{in}$ is the step function change in voltage as applied to terminal 99 and $C_{in}$ is the value of the input capacitance.

According to the prior art, the value $C_{in}$ was fixed so that $\Delta V_{in} \times C_{in}$ created a step function change of the amount of charge applied at node 16. Namely, the value $Q_{in}$ was always a known value for each cell and did not vary. On the other hand, if the body is used for $C_{in}$, when the body undergoes a step function $\Delta V_{in}$ the amount of charge provided at each individual cell will be different from that provided to other cells since the value locally at the individual cell will be different for each capacitor $C_{in}$. Accordingly, the amount of charge transferred to the input node 25 will also vary for each individual cell. As will be appreciated, the actual local capacitance of each individual cell will not be precisely known, and will vary over a wide range. For principles of the present invention, we can now consider two extremes, namely, the input capacitance of the valley $C_{valley}$ and the capacitance of a ridge at $C_{ridge}$. The capacitor $C_{in}$ will be at a maximum value while at a ridge with the skin in direct contact with the dielectric layer 11. On the other hand, $C_{in}$ will go down, and be at a minimum value while at a valley. This can be understood according to the equations $C_{in}$=min at valley and $C_{in}$=max at a ridge. Since the fingerprint pattern of an individual varies between ridge and valleys, it will be appreciated that the actual input capacitance will also vary somewhat from the two extremes of the minimum and maximum value.

Turning back now to FIG. 9, over the second cell 2b a valley is present. In this circumstance, the finger 18 is separated by a distance $d_2$ from the upper surface 125 of dielectric layer 11. Since a valley is curved, the actual shape may vary from a normal distance $d_2$ to a maximum distance and an intermediate distance. Taking the case in which the valley is quite large, there will be no interference between the fringe capacitive field lines 35 that extend between the plates 24 and 23 of the feedback capacitor to the negative amplifier 13. In particular, all of the fringe field lines 35 which existed between plates 24 and 23 still exist when the valley is adjacent the cell such that it does not interfere with the capacitance value in any way. The capacitance value $C_s$ is therefore at a maximum value for the presence of a valley. On the other hand, the input capacitance is represented by field lines 37 is at a minimum value. Namely, with the valley present and the finger 18 spaced a far distance from the plate 24, the input capacitance is very small, and for a large valley is at a minimum value. This is to be compared with the ridge of cell 2a at which the input capacitance was large and there were a large number of field lines 37, as shown.

FIG. 10 illustrates an electrical schematic showing equivalent circuit of some components which will exist under normal operating conditions. In particular, from an electrical equivalent standpoint, the input node 25 will have parasitic capacitor 41 coupled thereto. In addition, output node 17 will have a parasitic capacitor 43 coupled thereto. These parasitic capacitors $C_p$ will have an effect on the electrical operation of the circuit. Further, the electrical equivalent of the negative feedback amplifier 13 is a simple inverter 13, as shown in FIG. 7, assuming, the situation of an ideal negative amplifier with infinite gain. In this situation, a number of field lines 35 extend between plates 24 and 23 of the capacitor, which provides the negative feedback from the output 17 to the input 25. The field lines 37 represent the value and strength of the input capacitance provided from the body being used as the input capacitor. As previously described, there is applied to terminal 99 a step voltage $\Delta V_{in}$ and to terminal 21 a step voltage $\Delta V_c$ of opposite polarity type. The actual values of $\Delta V_{in}$ and $\Delta V_c$ are not of particular importance and in many circumstances, they will be a different value. In alternative embodiments, they are inverse signals of each other, such that they vary exactly the opposite in timing and in magnitude.

The plate 43 for the capacitance of the body as represented by the finger 18 in contact with the substrate 1. The step voltage $\Delta V_{in}$ is connected to capacitance of the body via Z BODY, as previously shown with respect to FIG. 6. When the body has a conductor, such as a portion of the skin which is very closely adjacent the plates 24 and 23 of the feedback capacitor, then the plate 43 of the capacitance of the body has a different effect than when the conductor of the body is spaced farther from the plates 24 and 23. In particular, when a ridge is present, then the input field lines 37 are significantly increased so that the capacitance 43 of the body and the overall body conductor has the effect of causing an increase in the input capacitance at node 25. At the same time, since the same body portion is adjacent the capacitor plates 24 and 23 for the same cell for which sensing is occurring, the same effect will cause a significant decrease in the field lines 35 passing from plates 24 and 23 as illustrated with respect to FIG. 6. Namely, the effect of using the body for both the input capacitance and sense capacitance will be opposite, in one case causing an increase in the input capacitance and in the other case causing a decrease in the sense capacitance. Since these two portions of the equations are a ratio with respect to each other, the overall sensitivity of the measurement is significantly enhanced. Similarly, if the body capacitance 43 has a valley adjacent the cell 2, it will have a reduced input capacitance represented by reduced field lines 37 and an increased capacitance between plates 24 and 23, since the valley does not interfere with the field lines 35, again shown in FIG. 6. The parasitic capacitance 41 and 43 thus have an overall reduced effect on the circuit.

Figure 11:
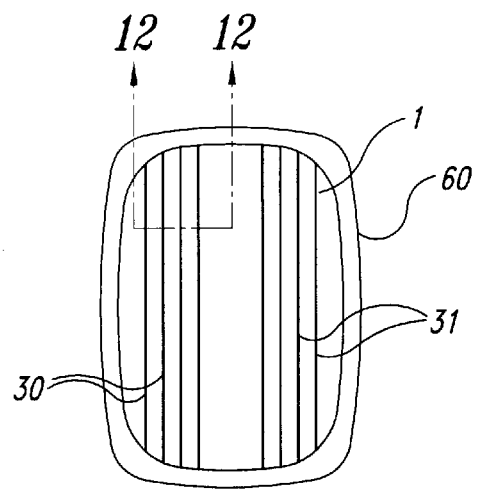
FIG. 11 is a top view of a housing containing a sensor according to the present invention.
Figure 12:
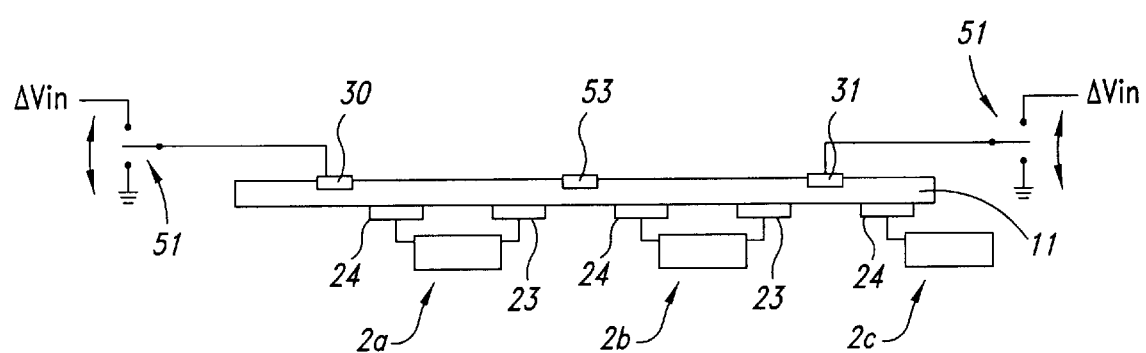
FIG. 12 is a partial cross-sectional view of the substrate of FIG. 11 taken along the lines 12—12.

FIGS. 11 and 12 illustrate one acceptable technique for placing the change in voltage $\Delta V_{in}$ on the human body while the fingerprint sensing is occurring. The substrate 1 is included within a housing 60. Positioned on the face of the substrate 1 are a plurality of electrical conductors 30, as shown in FIGS. 8 and 9. The conductors 30 and 31 are electrically conductive strips formed in the upper surface of the substrate 1. In particular, these electrical conductors will be in direct electrical contact with the finger 18 of the user that is placed on the substrate 1.

According to principles of the present invention, the electrical conductors 30 and 31 have applied thereto the step voltage $\Delta V_{in}$ or, a grounding voltage, depending on the timing of the sense operation and the location of the cell being sensed relative to the electrical conductors 30, 31. One set of conductors 30 has the step voltage $\Delta V_{in}$ applied thereto so as to place $\Delta V_{in}$ on the body, according to the timing sequences previously described. The other conductors are grounded, so as to ground the portion of the finger 18 which is not adjacent the cell being sensed. In this case, the resistance to ground 33 as shown in FIG. 6 is reduced to 0.

The operation of the circuit according to FIGS. 11 and 12 will be as follows. When a user places their finger on the substrate 1, a portion of the finger will be in contact with the array of wires 30, whereas another portion of the finger will be in contact with the array of wires 31. Underneath each of the grid of wires is the array 3 composed of a plurality of sensor cells 2. When sensing is being performed at a particular cell 2a as shown in FIG. 12, one of the array of wires, either 30 or 31 is coupled to ground and the other array is coupled to $\Delta V_{in}$. In a first embodiment, the grid closest to the cell, 30, will be coupled to ground, and the grid spaced further from the fringes, grid 31, will be coupled to $\Delta V_{in}$. In a second, alternative embodiment, the grid of wires which is adjacent that particular cell will be connected to $\Delta V_{in}$ by switch 51.

In the first embodiment, as $\Delta V_{in}$ varies from high to low, the electrical conductor 31 which is spaced from sensor cell 2 is in direct contact with the finger, so the finger will also track $\Delta V_{in}$. The other grid 30 will be coupled to ground so that the adjacent portion of the finger 18 is held at ground. Sensing will progress using circuits of any acceptable type, one of which uses the vertical and horizontal scan patterns shown in FIG. 1, but others may also be used. As the sensing progresses through the array, in each instance the localized grid of wires, whether 30 or 31 which is spaced from the cell 2 being sensed will be directly connected to $\Delta V_{in}$ so that the body voltage and that portion of the finger tracks the voltage $\Delta V_{in}$. The other portion of the grid will be connected to ground. Namely, when those cells which are underneath the grid 31 are being sensed, the grid 31 will be connected to $\Delta V_{in}$. Thereafter, when the cells which are under grid 31 are being sensed, grid 31 will be connected to ground, and grid 30 will be connected to $\Delta V_{in}$.

In the second embodiment, the grid adjacent the cell being sensed is coupled to $\Delta V_{in}$ and the grid spaced from the finger, or area around the periphery of the device is coupled to ground. See, for example, FIGS. 13, 14 and accompanying text in which there is a grounded conductor at the peripheral edge of the entire device.

Figure 13:
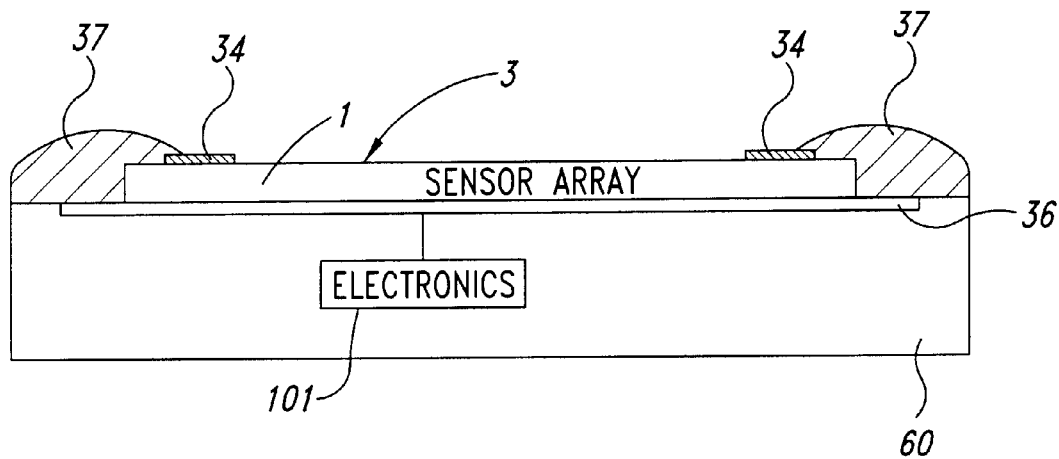
FIG. 13 is a partial cross-sectional view of a substrate and housing containing the invention.
Figure 14:
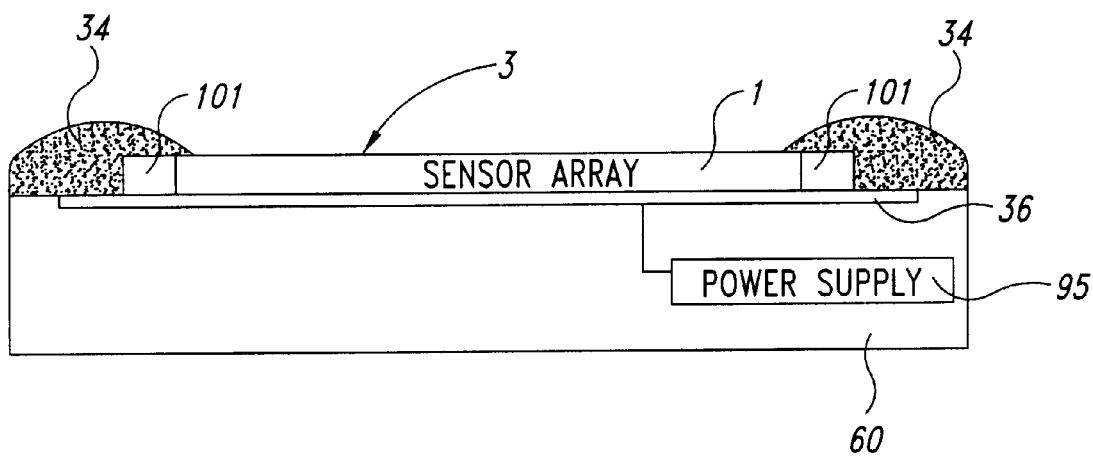
FIG. 14 is a partial cross-sectional view of an alternative substrate and housing of the present invention.

In the example shown in FIG. 11, there is a space distance between grids 30 and 31 so that they do not electrically interfere with each other. Since the difference between the first and second embodiments relates to whether the grid adjacent the fringe is connected to ground or to $\Delta V_{in}$, respectively, also applies to the description just given the second embodiment, with the locations reversed and thus it need not be repeated. As an alternative, there could be a third electrical grid around the edges or positioned between the two grids, as shown in FIGS. 13 and 14 or by the middle electrode 53 of FIG. 12, respectively. This third electrode can be placed at ground, coupled to $\Delta V_{in}$, or switched from $\Delta V_{in}$ to ground during the operation. Alternatively, it may be sufficient to have merely two voltage grids on or adjacent the substrate 11.

FIG. 13 illustrates a further alternative embodiment according to principles of the present invention. According to this embodiment, the housing 60 has contained therein a substrate 1 which includes the sensor array 3, as previously described. The substrate 1 has a sealing material 37 so as to provide a weatherproof and rugged package 60 for housing the substrate 1 with a sensor array 3 thereon. On an upper surface at an edge portion is provided conductors 32 and 34. The conductors 32 and 34 are directly adjacent, or in some instances overlapped by the sealing material 37. The conductors 32 and 34 are preferably not directly over portion of the sensor array. Instead, they are spaced sufficiently far from the array that they do not have an electrical impact on the capacitance value of each individual pixel within cell 2. In one embodiment, the conductor 32 is connected to $\Delta V_{in}$ during the entire sensing operation, and the conductor 34 is connected to ground. In this instance, the electrical conductor 32 provides the change in voltage $\Delta V_{in}$ for all of the cells 2 during sensing. Similarly, conductor 34 is always ground so as to ground a portion of the body such that $R_g$ is at or near 0. The output of each individual sensor cell 2 is provided so that the fingerprint sensing occurs as previously described.

In an alternative embodiment, the electrical conductors 32 and 34 are connected to each other so as to provide a conductive strip which is a continuous single strip all the way around the peripheral edge of the substrate 1 within the package 60. As can be appreciated, for preferred operation, the finger of the user is in contact at all times with either conductor 32 or conductor 34. Unfortunately, if the user moves their finger, they may come out of contact with one or two of the conductors and press into the other conductor. Since this would have a detrimental effect on the sensing capability, it may be preferred that the entire conductor surrounding the sensor array 3 be at the same voltage at all times so that if the person's finger moves, they can always be assured of being in contact with a known electrical voltage. In this instance, the conductive ring 32 and 34 are electrically connected to each other so that both are always held at the same voltage. According to principles of the present invention, the voltage will be $\Delta V_{in}$ so that the voltage on the human body is directly controlled during the sensing operation. In this instance, the resistance to ground is not controlled. Namely, resistor $R_g$ as shown in FIG. 3 becomes an unknown value.

FIG. 14 illustrates a conductive housing seal 34 for providing electrical connection to the finger. A conductive particle, such as carbon, iron, graphite, or the like is embedded into the sealing member 34 so that the voltage step can be applied to the housing 60 and it will be provided to the person's finger. The conductive epoxy is connected so as to not short out the lead lines, wire bonding, pad connectors, etc.

Figure 15A:
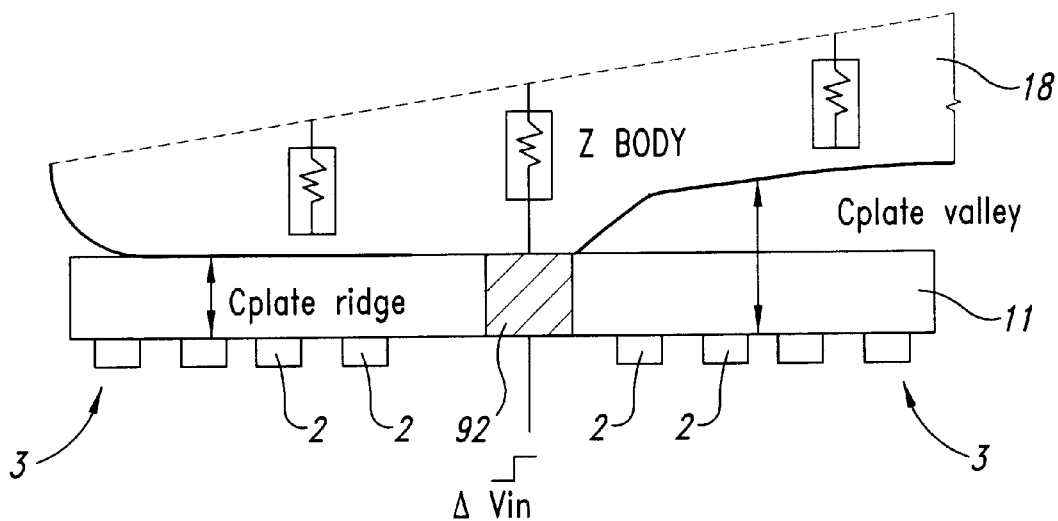
FIGS. 15A and 15B are side views of a further alternative embodiments to place a voltage change on the finger of the user.

FIG. 15A illustrates an additional structure for placing a voltage change on the person's finger 18. According to this embodiment, a large conductive metal line 92 is connected in the upper portion of the substrate so as to be in an electrical connection with the user's finger 18. (The individual electrical connections are not shown for simplicity.) A metal line 92 may be an array of lines, interspaced throughout the array and positioned between the individual cells 2 or positioned on the edge of the array, as shown in FIGS. 13 and 14. Thus, when a person places their finger on the finger print sensor, it automatically directly contacts the conductor 93. Charge can be injected into, or removed from, the person's finger by varying the voltage on the electrical conductor 92. With a large number of lines 92 spaced throughout the array, the user can be assured of having good electrical contact with a sufficient number of lines that the desired step voltage is placed on the person's finger during the sensing operation. Accordingly, while a single line is shown for purposes of illustration, it is understood that other lines in various patterns, such as a number of parallel lines, a grid or other pattern, may be positioned within the semiconductor substrate and having an exposed upper surface with a variable voltage source connected thereto.

Figure 15B:
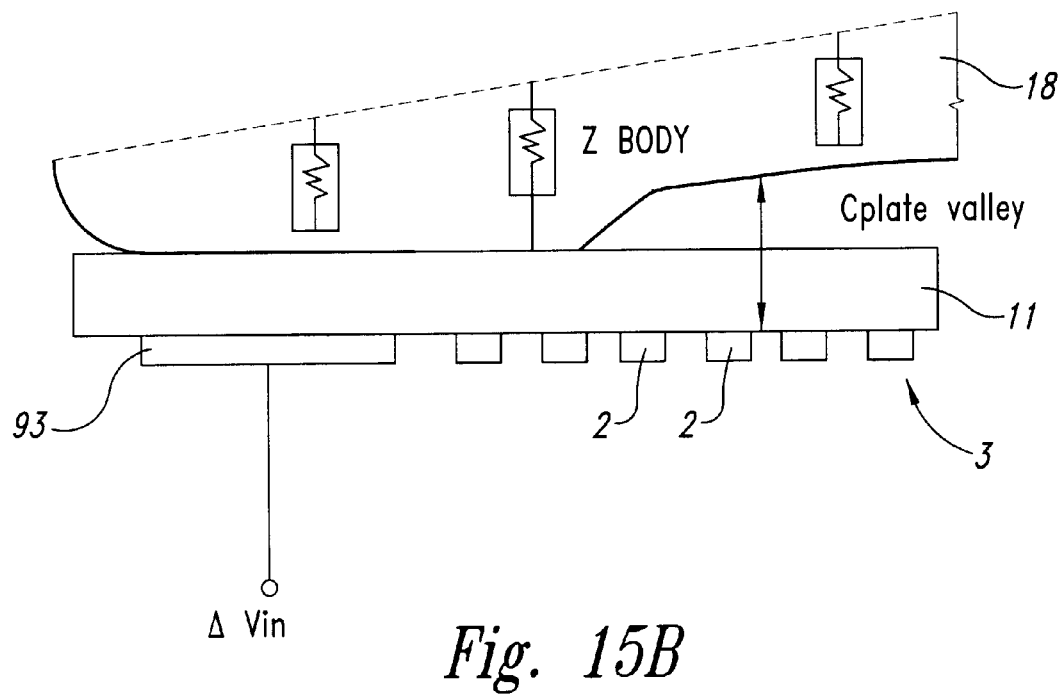

FIG. 15B illustrates a further circuit for placing a voltage change on the person's finger 18. A large plate of a capacitor is formed in the substrate. This is separate than and spaced away from the array 3 that is composed of sensor cells 2. (The individual electrical connections are not shown for simplicity.) The plate 93 of the charge transfer capacitor is connected to the input voltage, $\Delta V_{in}$. The finger of the user acts as the other plate of the input capacitor. In this case, the plate 93 of the input capacitor is very large, so that it covers many ridges and valleys. Its primary purpose is charge transfer, not sensing. When a voltage change $\Delta V_{in}$ is placed on this plate 93, the body, acting as the other plate of the capacitor, sees a step input voltage. The effect of this is sensed at the individual cells 2 in the manner described herein. An array of small capacitors interspersed throughout the array could also be used in place of the large one.

Figure 16A:
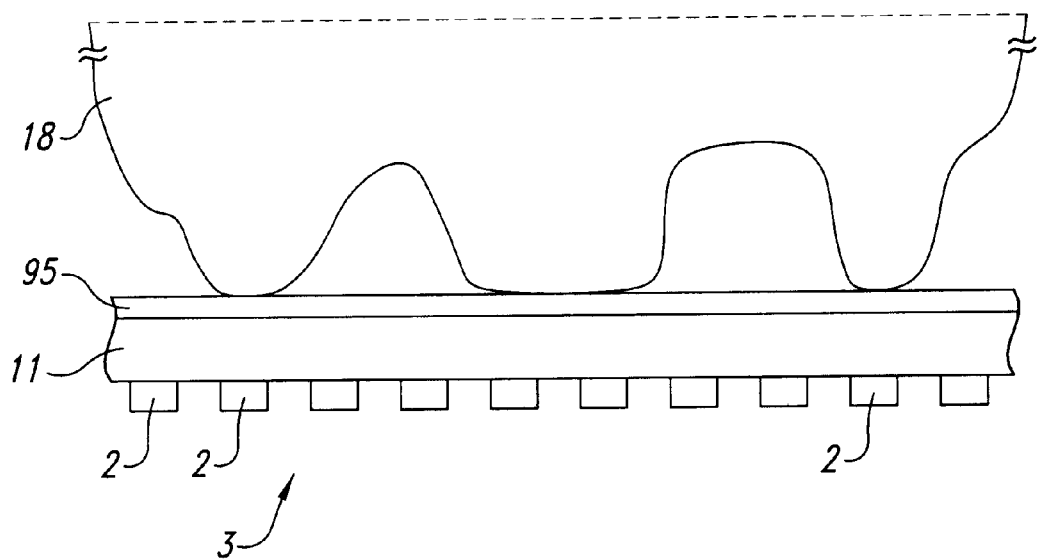
FIGS. 16A and 16B illustrate alternative interference mechanisms which may increase the difficulty of properly reading a fingerprint of a user.
Figure 16B:
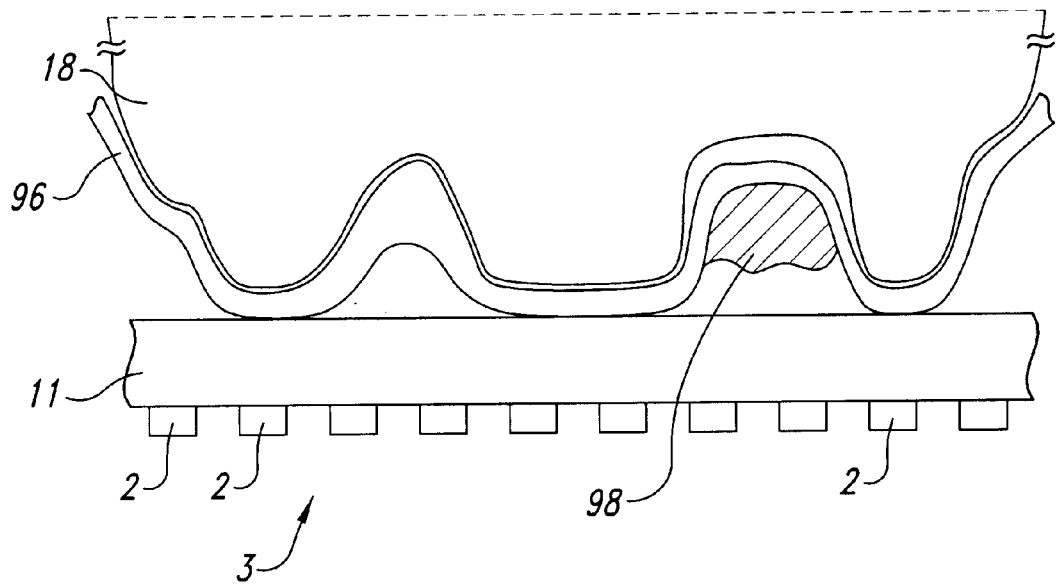

FIGS. 16A and 16B illustrate some practical applications of the present invention based on potential problems encountered in daily use. As can be appreciated, fingerprint sensors can be advantageously used in a daily routine. For example, a fingerprint sensor may be placed on a car door so that a person may push their thumb, or some other member having a fingerprint pattern against the car door, and upon being recognized be permitted to open the car door and operate the car. Similarly, a fingerprint sensor may be part of a remote car lock and unlock mechanism of the type shown and described in application Ser. No. 09/475,686, incorporated herein by reference. There are numerous other situations when sensing a fingerprint may be important, such as identification of individuals at various times during prison incarceration, a safety feature for a handgun to prohibit firing until the correct palm print or fingerprint has been placed thereon, to lock or unlock certain rooms to which restricted access is provided to only selected individuals, or other potential uses. Each of these uses, particularly those for an automobile and a safety device for a handgun, operate in relatively dirty environments. For example, a car may be parked outside, in adverse weather conditions for extended periods of time. In addition, the person wishing to drive the car may have dirt, grease, or other debris on their fingerprint which, under standard conditions, may interfere with the proper sensing of the fingerprint pattern. Further, the person may be wearing a glove, such as a thin glove composed of latex, neoprene, rubber, or other non-permeable, elastic membrane to provide a sterile working environment for the hand, as may often be the case in hospitals or other medical procedures. It is desirable to be able to sense a fingerprint pattern of a user even though their hands may be covered with dirt, debris, a thin glove or other membrane. The present invention has been found to be particularly useful in those environments which represent actual operating conditions for users, and daily work. FIGS. 16A and 16B illustrate two potential situations which may occur in practical use of the fingerprint sensor for which the present invention provides a solution.

FIG. 16A shows the dielectric substrate 11 having individual sensor cells 2 formed in the array 3 therein. A finger 11 of a user is positioned for placing on the dielectric layer 11. A layer 95 of foreign material is interposed between the dielectric layer 11 and the finger 18 of the user. The layer 95 may be any foreign material whose properties and even presence cannot reliably be predicted. It may include, for example, a drops, bits of ice which has frozen from a thin sheet of water, frost, snow, dirt or grime, or other foreign material which may build up on the dielectric 11 since the fingerprint sensor is exposed to outdoor weather conditions. Of course, it is desired that a user remove as much foreign debris and only layers of water, snow, ice and dirt before sensing. A large amount of foreign material, particularly if it is highly conductive, will make proper operations of the sensor difficult. The debris may also be local and positioned only over some sensor cells and not others, such as a small drop of rain, etc. It is desired to minimize or remove as much unplanned debris as possible, even so, some may be present. Thus, in one embodiment, the layer 95 represents a buildup of foreign debris based on the fingerprint sensor being in an outdoor environment for an extended period of time. In addition, the layer 95 may be a layer worn by the user. In some situations, the layer 95 may be a latex glove, a rubber glove, or some other protective layer which a user may be wearing. A glove with appear to the sensor to be a smooth, flat layer 95 on top of the dielectric surface. In one embodiment it may be an additional protective layer, such as wax paper, a thin plastic wrap coating, or other material which is positioned on top of the entire sensor array 3 in order to protect it from damage due to adverse weather and harsh environmental conditions. In such a situation, the layer 95 is a removable layer which may be taken off and replaced on a regular basis. Thus, the substrate 11 remains clean and free of debris, and the protective cover 95 is merely removed, discarded, and a new, clean coating 95 placed thereon to maintain the entire sensor in good operating condition.

For example, in one embodiment, the top of package 60, or potentially the entire package 60, including the substrate and sensor array 3, may be completely enclosed in a watertight, thin plastic layer. This will provide the advantage that the sensor array is sealed from a high-moisture or other harsh operating environment. The protective layer 95 is then replaced as needed. Accordingly, the layer 95 represents any layer of material which is positioned between the dielectric layer and the fingerprint on the finger 18 which is being sensed whether intentionally or not. As can be appreciated, the physical shape, electrical properties, and effect on capacitive sensing of the layer 95 cannot always be completely nor accurately predicted. In addition, it may change over time, particularly in those cases where the layer 95 represents a buildup of debris, or other temporary material which may be partially cleaned from the surface 11. Thus, for a period of time the sensor may operate having the finger 18 in direct contact with the substrate 11 and, in different situations the very same sensor may operate having some foreign material in the form of a layer 95 between the finger 18 and the dielectric layer 11.

FIG. 16B illustrates a layer 96 and debris 98 which has a different configuration than the layer 95 of FIG. 16A. In particular, the layer 96 is more conformal to the fingerprint pattern of the user, whereas the layer 95 is flat, and more conformal to the dielectric layer 11. Further, some material 98 may be intermittently positioned on the finger of a user either in a valley, on top or a ridge, or some other location. The material that adheres to the finger, in the form of layer 96 may be intermittent, or may have different thickness at different locations and may have air pockets under the material, such as the air pocket under debris 98. Examples of material 96 include such items as a thin layer of oil on a person's thumb which may build up slowly during the day due to normal bodily functions. It may, alternatively, be a drop of water, which may be perspiration, wet hands from a raindrop, or some other thin coating 96 which is generally conformal to the person's finger, but in fact may only partially follow the ridges and valleys of the thumbprint, based, of course, on the properties of the layer 96. Debris 98 is of the type which may occur when the user has been in a harsh working environment, such as working in the field and having dirt, grime, grease, or some other material which has adhered to their finger. In the event the sensor is used on a handgun to sense the identity of the palm print of a user, it may very well be the residue from handling the gun and loading it, such as the oil from the gun, gunpowder, small flakes of lead, or other debris which often adheres to a person's finger during such activities. Thus, the material 98 may appear in various pockets on different parts of the person's hand, and may or may not be conformal to the hand depending on the type of debris.

The present invention is particularly applicable to use of the invention in the embodiments of FIGS. 16A and 16B, in which additional material, whose properties may not be totally predictable, are positioned over the dielectric layer 11 between the finger of the user. The terminal 99 is coupled to the body of the user through any acceptable technique, whether capacitive coupling is shown in FIG. 15B, coupling to the other hand of the user, some other body part, or to the finger itself. The present invention, by increasing the sensitivity of the distinction between the ridges and valleys as described in the equations briefly herein, is able to more distinctly and accurately sense the difference between a ridge and a valley. The circuit of the present invention is therefore useful for outputting the relative differences between the effect of a ridge or a valley on the fingerprint sensor rather than the absolute values of each. The circuit of the present invention is particularly useful for producing a signal which distinguishes a ridge from a valley within a fingerprint, since the relative effect of each is amplified using the circuit of the present invention as has been previously explained herein.

Figure 17:
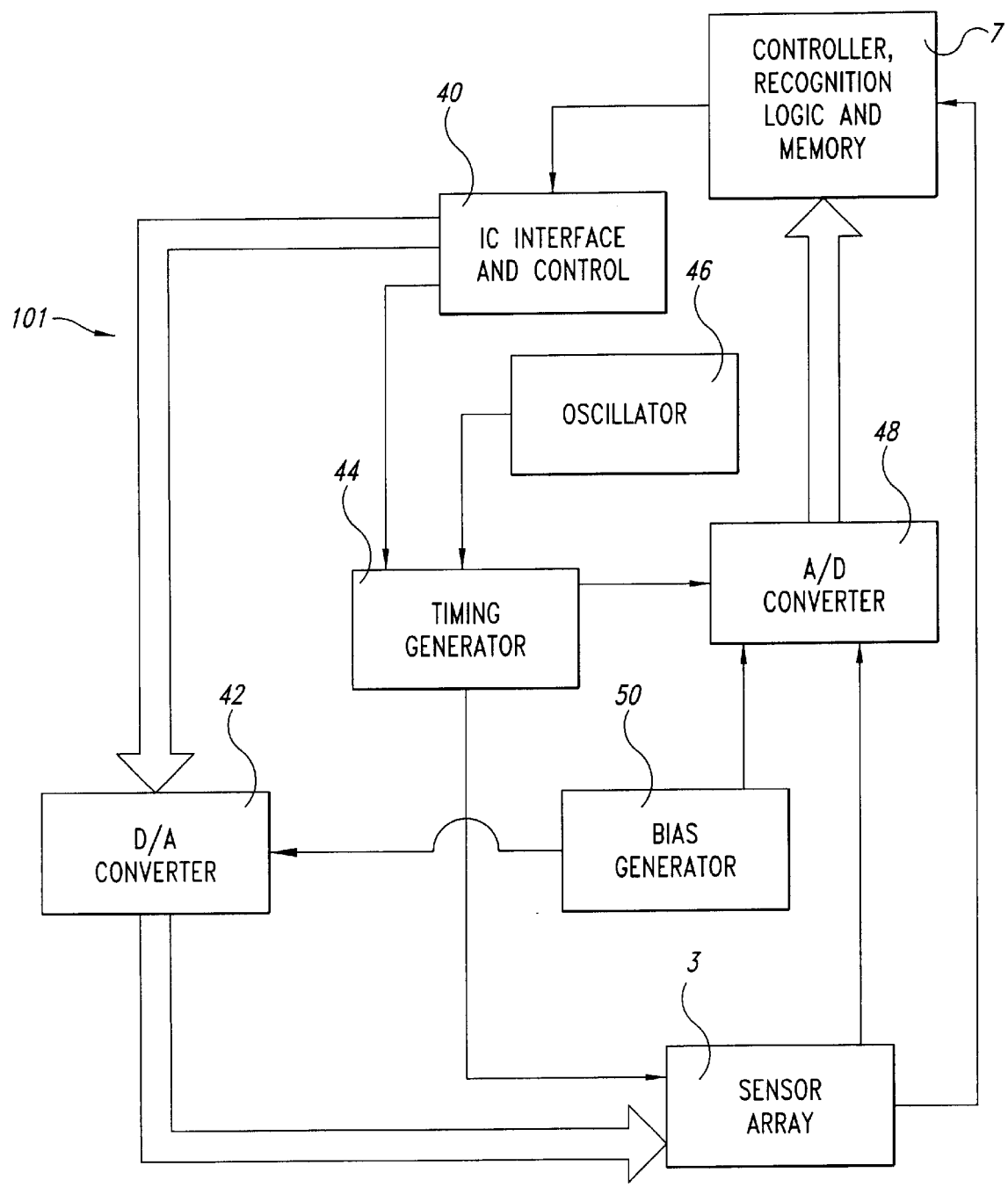
FIG. 17 is an electrical schematic of the circuit according to principles of the present invention.

FIG. 17 illustrates the electronics 101 which may be used in controlling the present invention. The electronics 101 may be positioned within a package 60 directly under the sensor array 3 as shown in FIG. 13. Alternatively, the electronics 101 may be positioned in the same semiconductor substrate as the sensor array 3 and positioned in a peripheral region such that the control electronics are included in the same integrated circuit as the entire sensor array, as shown in FIG. 15. The electronics 101 include the sensor array 3, and the appropriate clocks, electronic controllers, and interface, together with the memory and recognition logic for proper operation of the fingerprint sensor. For example, coupled as an output to the sensor array 3 may be a A/D converter 48 whose output is provided to the controller, recognition and logic 7, also shown in FIG. 1. The integrated circuit interface circuit 40 receives signals from the controller 7 and provides output to the appropriate circuits, such as a D/A converter 42 and a timing generator 44. A bias generator 50, as well as an oscillator 46 are coupled to the appropriate circuits for providing the correct bias voltages as well as clock circuits as needed. The integrated circuit interface circuit 40 also includes the appropriate I/O circuits so as to output a signal indicating that a valid match has been found, or an invalid match has been found. After the integrated circuit interface 40 has output the results of the match, then the appropriate action can be enabled based on the results of the match. For example, if a valid match, it may enable starting the car, opening the door, access to the bank account, the firing of a handgun or some other activity. On the other hand, if a valid match is not found then the interface circuit may put out the appropriate signal to block any further activity, send an alert signal to a security system indicating that an unauthorized user has attempted access, or perform other functions as desired.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A fingerprint detection apparatus comprising:
   a capacitive sensor cell for sensing a fingerprint pattern;
   a voltage output terminal adapted to be coupled to the body of a person whose fingerprint pattern in being detected;
   a switch for selectively providing a first voltage potential and a second voltage potential to the voltage output terminal sequentially while the fingerprint pattern is being detected.

2. The fingerprint detection apparatus according to claim 1 wherein the voltage output terminal is a conductive metal strip positioned adjacent the capacitive sensor cell.

3. The fingerprint detection apparatus according to claim 1 further including:
   a substrate composed of silicon;
   an integrated circuit formed in said substrate; and
   a dielectric layer as a top layer of the integrated circuit, the top surface of the dielectric layer being exposed for receiving said fingerprint pattern, the capacitive sensor cell being formed as part of the integrated circuit.

4. The fingerprint detection apparatus according to claim 3 wherein the voltage output terminal includes a first set of a metal strips located in a top surface of the dielectric layer.

5. The fingerprint detection apparatus according to claim 3 further including:

first set of metal strips located at the top layer of the dielectric layer;

a second set of metal strips located at the top layer of the dielectric layer;

a control circuit for selecting either the first set of metal strips to be the voltage output terminal or the second set to be the voltage output terminal and the second set of metal strips to be coupled to a ground voltage potential.

6. The fingerprint detection apparatus according to claim 3 further including:

a layer of material over the dielectric layer that is the top layer of the integrated circuit.

7. The fingerprint detection apparatus according to claim 3 further including:

a water tight protective layer enclosing the entire detection apparatus, including the substrate and the dielectric layer.

8. The fingerprint detection apparatus according to claim 1 further including:

a ground terminal positioned adjacent the capacitive sensor cell for coupling a finger placed thereon to ground during sensing of the fingerprint pattern.

9. The fingerprint detection apparatus according to claim 1 wherein said capacitive sensor cell includes a single plate of a capacitor and the finger, if present, provides a second plate of a capacitor for the cell.

10. The fingerprint detection apparatus according to claim 1 wherein said capacitive sensor cell includes a first plate of a capacitor, a second plate of a capacitor and the finger, if present, provides a third plate of a capacitor for the cell.

11. The fingerprint detection apparatus according to claim 10 further including an inverting amplifier having an input coupled to one plate of the capacitor and an output coupled to the second plate of the capacitor.

12. The fingerprint detection apparatus according to claim 11 further including:

an input compensation capacitor having the first plate coupled to the input of the inverting amplifier and the second plate coupled to a compensation voltage terminal;

a second switch for selectively providing a third voltage potential and a fourth voltage potential to the compensation voltage output terminal sequentially while the fingerprint pattern is being detected.

13. The fingerprint detection apparatus according to claim 12 wherein the first switch and the second switch are controlled by the same clock signal such that they switch to the different voltage potentials at the same time.

14. The fingerprint detection apparatus according to claim 12 wherein the first voltage potential is a low value and the second voltage potential is a high value such that the electrical potential on the body is switched from low to high during sensing.

15. The fingerprint detection apparatus according to claim 12 wherein the third voltage potential is a high value and the fourth voltage potential is a low value such that the input signal to the inverting amplifier is switched from high to low during sensing.

16. The fingerprint detection apparatus according to claim 1 wherein the first voltage potential is a low value and the second voltage potential is a high value such that the electrical potential on the body is switched from low to high during sensing.

17. The fingerprint detection apparatus according to claim 1 further including:

a finger of a user positioned for having the fingerprint sensed;

a glove on the finger of the user during sensing of the fingerprint.

18. A method of sensing a fingerprint pattern comprising:

placing a finger adjacent a fingerprint sensor cell;

coupling the finger to an electrical power supply;

sensing the fingerprint pattern; and changing the voltage on the finger during sensing of the fingerprint pattern.

19. The method according to claim 18 further including:

placing a glove on the finger prior to placing the finger adjacent the sensor cell.

20. The method according to claim 18 further including:

placing a protective layer on the sensor cell prior to placing the finger adjacent the sensor cell.

21. The method according to claim 20 further including:

periodically removing the protective layer on the sensor cell and placing a different protective layer on the sensor cell to maintain a clean top surface of the sensor cell.

22. The method according to claim 18 further including:

coupling the fingerprint sensor cell to a variable voltage electrical power supply;

sensing the fingerprint pattern; and changing the voltage provide by the variable voltage power supply on the sensor cell during sensing of the fingerprint pattern.

* * * * *

(12) EX PARTE REEXAMINATION CERTIFICATE (10230th)

United States Patent
Kramer

(10) Number: US 6,512,381 C1
(45) Certificate Issued: Jul. 24, 2014

(54) ENHANCED FINGERPRINT DETECTION

(75) Inventor: Alan Kramer, Berkeley, CA (US)

(73) Assignee: Authentec, Inc., Melbourne, FL (US)

Reexamination Request:
No. 90/012,951, Aug. 14, 2013

Reexamination Certificate for:
Patent No.: 6,512,381
Issued: Jan. 28, 2003
Appl. No.: 09/753,344
Filed: Dec. 29, 2000

Related U.S. Application Data

(63) Continuation-in-part of application No. 09/475,351, filed on Dec. 30, 1999, now abandoned.

(51) Int. Cl.
*A61B 5/117* (2006.01)
*G06K 9/00* (2006.01)

(52) U.S. Cl.
USPC .......................................... 324/658; 324/661

(58) Field of Classification Search
None
See application file for complete search history.

(56) References Cited

To view the complete listing of prior art documents cited during the proceeding for Reexamination Control Number 90/012,951, please refer to the USPTO's public Patent Application Information Retrieval (PAIR) system under the Display References tab.

*Primary Examiner* — B. James Peikari

(57) ABSTRACT

An enhanced fingerprint sensing circuit in which a voltage change is applied to the body during sensing. When the person's fingerprint is being sensed, the person's body is in contact with an electrical terminal. When the sensing occurs, the voltage on the electrical terminal changes, which changes the voltage on the person's body. The pattern of the fingerprint performs two functions in the sensing circuit. In addition to being a plate of a capacitor whose distance is being sensed, it is now a source of input charge as well. The electrical effect on the cell of a voltage change on a person's finger is different at a ridge than at a valley in the fingerprint sensing circuit. Thus, the input capacitance to the sensing circuit is variable, depending upon whether a ridge or a valley is present. The sensing circuit also detects a change in its own capacitance based on the presence of a ridge or a valley. In summary, the person's body acts as the input capacitor to provide a variable charge transfer for the input capacitance and at the same time performs the function of being a variable sensing capacitor value for the capacitive sensor. The fingerprint sensor is thus very sensitive and can detect a person's fingerprint even if a protective layer, such as plastic, wax paper or the like is over the sensor. In addition, if the person is wearing a thin glove, such as a latex glove, the fingerprint patterns can still be sensed.

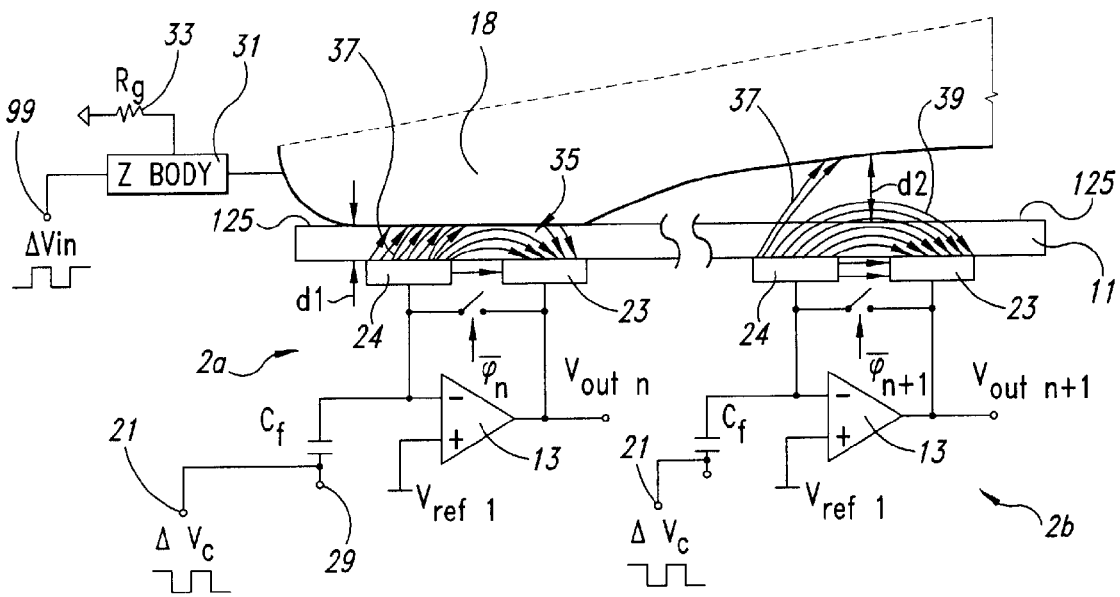

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3, 9, 16, 18, 20 and 22 are cancelled.

New claims 23-141 are added and determined to be patentable.

Claims 2, 4-8, 10-15, 17, 19 and 21 were not reexamined.

23. *A fingerprint detection apparatus comprising:*
   *a capacitive sensor cell for sensing a fingerprint pattern;*
   *a voltage output terminal adapted to be conductively coupled to the body of a person whose fingerprint pattern is being detected;*
   *a switch for selectively providing a first voltage potential and a second voltage potential to the voltage output terminal sequentially while the fingerprint pattern is being detected; and*
   *a charge measurement circuit for measuring a value related to a charge resulting from the fingerprint pattern being detected.*

24. *The fingerprint detection apparatus according to claim 23, wherein the voltage output terminal is separate from the capacitive sensor cell.*

25. *The fingerprint detection apparatus according to claim 23, wherein the value is a voltage related to a charge stored.*

26. *The fingerprint detection apparatus according to claim 23, wherein the value is a voltage related to a rate of change in a charge stored.*

27. *The fingerprint detection apparatus according to claim 23,*
   *wherein the capacitive sensor cell comprises a first plate selectively coupled by a reset switch to a second plate, and*
   *wherein the reset switch is configured to open to an opened position from a closed position, before the switch sequentially provides the first voltage potential and the second voltage potential.*

28. *The fingerprint detection apparatus according to claim 27, wherein the switch and the reset switch are configured to switch based on the same clock signal.*

29. *The fingerprint detection apparatus according to claim 27, wherein the reset switch is configured to close to the closed position from the open position, after the switch sequentially provides the first voltage potential and the second voltage potential.*

30. *The fingerprint detection apparatus according to claim 29, wherein the first voltage potential is a higher voltage than the second voltage potential.*

31. *The fingerprint detection apparatus according to claim 29, wherein the first voltage potential is a lower voltage than the second voltage potential.*

32. *The fingerprint detection apparatus according to claim 31, wherein the reset switch is configured to close while the switch is providing the second voltage potential.*

33. *The fingerprint detection apparatus according to claim 23,*
   *wherein the capacitive sensor cell comprises a first plate selectively coupled by a reset switch to a second plate, and*
   *wherein the reset switch is configured to close to a closed position from an open position, after the switch sequentially provides the first voltage potential and the second voltage potential.*

34. *The fingerprint detection apparatus according to claim 33, wherein the first voltage potential is a higher voltage than the second voltage potential.*

35. *The fingerprint detection apparatus according to claim 33, wherein the first voltage potential is a lower voltage than the second voltage potential.*

36. *The fingerprint detection apparatus according to claim 35, wherein the reset switch is configured to close while the switch is providing the second voltage potential.*

37. *The fingerprint detection apparatus according to claim 33, wherein the reset switch is configured to open to the opened position from the closed position, before the switch sequentially provides the first voltage potential and the second voltage potential.*

38. *The fingerprint detection apparatus according to claim 37, wherein the switch and the reset switch are configured to switch based on the same clock signal.*

39. *The fingerprint detection apparatus according to claim 23, wherein the voltage output terminal includes a continuous conductive strip surrounding the capacitive sensor cell.*

40. *The fingerprint detection apparatus according to claim 23, further including:*
   *a substrate composed of silicon;*
   *an integrated circuit formed in said substrate; and*
   *a dielectric layer as a top layer of the integrated circuit, the top surface of the dielectric layer being exposed for receiving said fingerprint pattern, the capacitive sensor cell being formed as part of the integrated circuit.*

41. *The fingerprint detection apparatus according to claim 23, wherein said capacitive sensor cell includes a single plate of a capacitor and the finger, if present, provides a second plate of a capacitor for the cell.*

42. *The fingerprint detection apparatus according to claim 23, wherein the first voltage potential is a low value and the second voltage potential is a high value such that the electrical potential on the body is switched from low to high during sensing.*

43. *A fingerprint detection apparatus comprising:*
   *a capacitive sensor cell for sensing a fingerprint pattern, wherein the capacitive sensor cell comprises a first plate and a second plate;*
   *a voltage output terminal adapted to be conductively coupled to the body of a person whose fingerprint pattern is being detected;*
   *a switch for selectively providing a first voltage potential and a second voltage potential to the voltage output terminal sequentially while the fingerprint pattern is being detected; and*
   *a reset switch for selectively coupling the first plate and the second plate,*
   *wherein the reset switch is configured to open to an opened position from a closed position, before the switch sequentially provides the first voltage potential and the second voltage potential.*

44. *The fingerprint detection apparatus according to claim 43, wherein the voltage output terminal is separate from the capacitive sensor cell.*

45. The fingerprint detection apparatus according to claim 44, wherein the switch and the reset switch are configured to switch based on the same clock signal.

46. The fingerprint detection apparatus according to claim 44, wherein the reset switch is configured to close to the closed position from the open position, after the switch sequentially provides the first voltage potential and the second voltage potential.

47. The fingerprint detection apparatus according to claim 46, wherein the first voltage potential is a higher voltage than the second voltage potential.

48. The fingerprint detection apparatus according to claim 46, wherein the first voltage potential is a lower voltage than the second voltage potential.

49. The fingerprint detection apparatus according to claim 48, wherein the reset switch is configured to close while the switch is providing the second voltage potential.

50. The fingerprint detection apparatus according to claim 49, further including:
a charge measurement circuit for measuring a value related to a charge resulting from the fingerprint pattern being detected.

51. The fingerprint detection apparatus according to claim 50, wherein the value is a voltage related to a charge stored.

52. The fingerprint detection apparatus according to claim 50, wherein the value is a voltage related to a rate of change in a charge stored.

53. The fingerprint detection apparatus according to claim 44, wherein the voltage output terminal includes a continuous conductive strip surrounding the capacitive sensor cell.

54. The fingerprint detection apparatus according to claim 44, further including:
a substrate composed of silicon;
an integrated circuit formed in said substrate; and
a dielectric layer as a top layer of the integrated circuit, the top surface of the dielectric layer being exposed for receiving said fingerprint pattern, the capacitive sensor cell being formed as part of the integrated circuit.

55. The fingerprint detection apparatus according to claim 44, wherein said capacitive sensor cell includes a single plate of a capacitor and the finger, if present, provides a second plate of a capacitor for the cell.

56. The fingerprint detection apparatus according to claim 44, wherein the first voltage potential is a low value and the second voltage potential is a high value such that the electrical potential on the body is switched from low to high during sensing.

57. A fingerprint detection apparatus comprising:
a capacitive sensor cell for sensing a fingerprint pattern, wherein the capacitive sensor cell comprises a first plate and a second plate;
a voltage output terminal adapted to be conductively coupled to the body of a person whose fingerprint pattern is being detected;
a switch for selectively providing a first voltage potential and a second voltage potential to the voltage output terminal sequentially while the fingerprint pattern is being detected; and
a reset switch for selectively coupling the first plate and the second plate,
wherein the reset switch is configured to close to the closed position from the open position, after the switch sequentially provides the first voltage potential and the second voltage potential.

58. The fingerprint detection apparatus according to claim 57, wherein the voltage output terminal is separate from the capacitive sensor cell.

59. The fingerprint detection apparatus according to claim 58, wherein the first voltage potential is a higher voltage than the second voltage potential.

60. The fingerprint detection apparatus according to claim 58, wherein the first voltage potential is a lower voltage than the second voltage potential.

61. The fingerprint detection apparatus according to claim 60, wherein the reset switch is configured to close while the switch is providing the second voltage potential.

62. The fingerprint detection apparatus according to claim 58, wherein the reset switch is configured to open to the opened position from the closed position, before the switch sequentially provides the first voltage potential and the second voltage potential.

63. The fingerprint detection apparatus according to claim 58, wherein the switch and the reset switch are configured to switch based on the same clock signal.

64. The fingerprint detection apparatus according to claim 58, further including:
a charge measurement circuit for measuring a value related to a charge resulting from the fingerprint pattern being detected.

65. The fingerprint detection apparatus according to claim 64, wherein the value is a voltage related to a charge stored.

66. The fingerprint detection apparatus according to claim 64, wherein the value is a voltage related to a rate of change in a charge stored.

67. The fingerprint detection apparatus according to claim 58, wherein the voltage output terminal includes a continuous conductive strip surrounding the capacitive sensor cell.

68. The fingerprint detection apparatus according to claim 58, further including:
a substrate composed of silicon;
an integrated circuit formed in said substrate; and
a dielectric layer as a top layer of the integrated circuit, the top surface of the dielectric layer being exposed for receiving said fingerprint pattern, the capacitive sensor cell being formed as part of the integrated circuit.

69. The fingerprint detection apparatus according to claim 58, wherein said capacitive sensor cell includes a single plate of a capacitor and the finger, if present, provides a second plate of a capacitor for the cell.

70. The fingerprint detection apparatus according to claim 58, wherein the first voltage potential is a low value and the second voltage potential is a high value such that the electrical potential on the body is switched from low to high during sensing.

71. A fingerprint detection apparatus comprising:
a capacitive sensor cell for sensing a fingerprint pattern, wherein the capacitive sensor cell comprises a first plate and a second plate;
a voltage output terminal adapted to be conductively coupled to the body of a person whose fingerprint pattern is being detected;
a switch for selectively providing a first voltage potential and a second voltage potential to the voltage output terminal sequentially while the fingerprint pattern is being detected; and
a reset switch for selectively coupling the first plate and the second plate,
wherein the switch and the reset switch are configured to switch based on the same clock signal, and
wherein the switch and the reset switch are configured to switch at different times.

72. The fingerprint detection apparatus according to claim 71, wherein the voltage output terminal is separate from the capacitive sensor cell.

73. The fingerprint detection apparatus according to claim 72, wherein the reset switch is configured to close to a closed position from an open position, after the switch sequentially provides the first voltage potential and the second voltage potential.

74. The fingerprint detection apparatus according to claim 73, wherein the first voltage potential is a higher voltage than the second voltage potential.

75. The fingerprint detection apparatus according to claim 73, wherein the first voltage potential is a lower voltage than the second voltage potential.

76. The fingerprint detection apparatus according to claim 75, wherein the reset switch is configured to close while the switch is providing the second voltage potential.

77. The fingerprint detection apparatus according to claim 72, wherein the reset switch is configured to open to the opened position from the closed position, before the switch sequentially provides the first voltage potential and the second voltage potential.

78. The fingerprint detection apparatus according to claim 72, further including:
a charge measurement circuit for measuring a value related to a charge resulting from the fingerprint pattern being detected.

79. The fingerprint detection apparatus according to claim 78, wherein the value is a voltage related to the charge.

80. The fingerprint detection apparatus according to claim 78, wherein the value is a change in voltage related to a change in the charge.

81. The fingerprint detection apparatus according to claim 72, wherein the reset switch is configured to open to an opened position from a closed position, before the switch sequentially provides the first voltage potential and the second voltage potential.

82. The fingerprint detection apparatus according to claim 81, wherein the reset switch is configured to close to the closed position from the open position, after the switch sequentially provides the first voltage potential and the second voltage potential.

83. The fingerprint detection apparatus according to claim 82, wherein the first voltage potential is a higher voltage than the second voltage potential.

84. The fingerprint detection apparatus according to claim 82, wherein the first voltage potential is a lower voltage than the second voltage potential.

85. The fingerprint detection apparatus according to claim 84, wherein the reset switch is configured to close while the switch is providing the second voltage potential.

86. The fingerprint detection apparatus according to claim 72, wherein the voltage output terminal includes a continuous conductive strip surrounding the capacitive sensor cell.

87. The fingerprint detection apparatus according to claim 72, further including:
a substrate composed of silicon;
an integrated circuit formed in said substrate; and
a dielectric layer as a top layer of the integrated circuit, the top surface of the dielectric layer being exposed for receiving said fingerprint pattern, the capacitive sensor cell being formed as part of the integrated circuit.

88. The fingerprint detection apparatus according to claim 72, wherein said capacitive sensor cell includes a single plate of a capacitor and the finger, if present, provides a second plate of a capacitor for the cell.

89. The fingerprint detection apparatus according to claim 72, wherein the first voltage potential is a low value and the second voltage potential is a high value such that the electrical potential on the body is switched from low to high during sensing.

90. A fingerprint detection apparatus comprising:
a capacitive sensor cell for sensing a fingerprint pattern;
a voltage output terminal adapted to be conductively coupled to the body of a person whose fingerprint pattern is being detected, wherein the voltage output terminal is separate from the capacitive sensor cell;
a switch for selectively providing a first voltage potential and a second voltage potential to the voltage output terminal sequentially while the fingerprint pattern is being detected; and
a charge measurement circuit for measuring a value related to a charge resulting from the fingerprint pattern being detected.

91. The fingerprint detection apparatus according to claim 90, wherein the value is a voltage related to a charge stored.

92. The fingerprint detection apparatus according to claim 90, wherein the value is a voltage related to a rate of change in a charge stored.

93. The fingerprint detection apparatus according to claim 90,
wherein the capacitive sensor cell comprises a first plate selectively coupled by a reset switch to a second plate, and
wherein the reset switch is configured to open to an opened position from a closed position, before the switch sequentially provides the first voltage potential and the second voltage potential.

94. The fingerprint detection apparatus according to claim 93, wherein the switch and the reset switch are configured to switch based on the same clock signal.

95. The fingerprint detection apparatus according to claim 93, wherein the reset switch is configured to close to the closed position from the open position, after the switch sequentially provides the first voltage potential and the second voltage potential.

96. The fingerprint detection apparatus according to claim 94, wherein the first voltage potential is a higher voltage than the second voltage potential.

97. The fingerprint detection apparatus according to claim 94, wherein the first voltage potential is a lower voltage than the second voltage potential.

98. The fingerprint detection apparatus according to claim 97, wherein the reset switch is configured to close while the switch is providing the second voltage potential.

99. The fingerprint detection apparatus according to claim 90,
wherein the capacitive sensor cell comprises a first plate selectively coupled by a reset switch to a second plate, and
wherein the reset switch is configured to close to a closed position from an open position, after the switch sequentially provides the first voltage potential and the second voltage potential.

100. The fingerprint detection apparatus according to claim 99, wherein the first voltage potential is a higher voltage than the second voltage potential.

101. The fingerprint detection apparatus according to claim 99, wherein the first voltage potential is a lower voltage than the second voltage potential.

102. The fingerprint detection apparatus according to claim 101, wherein the reset switch is configured to close while the switch is providing the second voltage potential.

103. The fingerprint detection apparatus according to claim 99, wherein the reset switch is configured to open to the opened position from the closed position, before the switch sequentially provides the first voltage potential and the second voltage potential.

104. The fingerprint detection apparatus according to claim 103, wherein the switch and the reset switch are configured to switch based on the same clock signal.

105. The fingerprint detection apparatus according to claim 90, wherein the voltage output terminal includes a continuous conductive strip surrounding the capacitive sensor cell.

106. The fingerprint detection apparatus according to claim 90, further including:
a substrate composed of silicon;
an integrated circuit formed in said substrate; and
a dielectric layer as a top layer of the integrated circuit, the top surface of the dielectric layer being exposed for receiving said fingerprint pattern, the capacitive sensor cell being formed as part of the integrated circuit.

107. The fingerprint detection apparatus according to claim 90, wherein said capacitive sensor cell includes a single plate of a capacitor and the finger, if present, provides a second plate of a capacitor for the cell.

108. The fingerprint detection apparatus according to claim 90, wherein the first voltage potential is a low value and the second voltage potential is a high value such that the electrical potential on the body is switched from low to high during sensing.

109. A method of sensing a fingerprint pattern comprising:
placing a finger adjacent a fingerprint sensor cell;
conductively coupling the finger to an electrical power supply;
sensing the fingerprint pattern; and
changing the voltage on the finger during sensing of the fingerprint pattern,
wherein sensing the fingerprint pattern comprises measuring a value related to a charge resulting from placing the finger adjacent the fingerprint sensor cell.

110. The method according to claim 109, wherein conductively coupling the finger to the electrical power supply comprises conductively coupling the finger to a voltage output terminal coupled to the electrical power supply, and wherein the voltage output terminal is separate from the fingerprint sensor cell.

111. The method according to claim 110, wherein the value is a voltage related to a charge stored.

112. The method according to claim 110, wherein the value is a voltage related to a rate of change in a charge stored.

113. The method according to claim 110, further including:
resetting the fingerprint sensor cell, before changing the voltage on the finger,
wherein the fingerprint sensor cell comprises a first plate and a second plate, and
wherein resetting comprises coupling and then uncoupling the first plate and the second plate.

114. The method according to claim 113, wherein resetting and changing the voltage on the finger are based on the same clock signal.

115. The method according to claim 113, further including:
coupling the first plate of the fingerprint sensor cell and the second plate of the fingerprint sensor cell, after changing the voltage on the finger.

116. The method according to claim 110, further including:
resetting the fingerprint sensor cell, after changing the voltage on the finger,
wherein the fingerprint sensor cell comprises a first plate and a second plate, and
wherein resetting comprises coupling and then uncoupling the first plate and the second plate.

117. The method according to claim 116, wherein resetting and changing the voltage on the finger are based on the same clock signal.

118. The method according to claim 110,
wherein coupling the finger to the electrical power supply comprises coupling the finger to a continuous conductive strip coupled to the electrical power supply, and
wherein the continuous conductive strip surrounds the fingerprint sensor cell.

119. The method according to claim 110, further including:
placing a protective layer on the sensor cell prior to placing the finger adjacent the sensor cell.

120. The method according to claim 110, further including:
coupling the fingerprint sensor cell to a variable voltage electrical power supply;
sensing the fingerprint pattern; and
changing the voltage provided by the variable voltage power supply on the sensor cell during sensing of the fingerprint pattern.

121. A method of sensing a fingerprint pattern comprising:
placing a finger adjacent a fingerprint sensor cell, wherein the fingerprint sensor cell comprises a first plate and a second plate;
conductively coupling the finger to an electrical power supply;
sensing the fingerprint pattern;
changing the voltage on the finger during sensing of the fingerprint pattern; and
resetting the fingerprint sensor cell, before changing the voltage on the finger,
wherein the fingerprint sensor cell comprises a first plate and a second plate, and
wherein resetting comprises coupling and then uncoupling the first plate and the second plate.

122. The method according to claim 121,
wherein conductively coupling the finger to the electrical power supply comprises conductively coupling the finger to a voltage output terminal coupled to the electrical power supply, and
wherein the voltage output terminal is separate from the fingerprint sensor cell.

123. The method according to claim 122, wherein resetting and changing the voltage on the finger are based on the same clock signal.

124. The method according to claim 122, further including:
coupling the first plate of the fingerprint sensor cell and the second plate of the fingerprint sensor cell, after changing the voltage on the finger.

125. The method according to claim 122, wherein sensing the fingerprint pattern comprises measuring a value related to a charge resulting from placing the finger adjacent the fingerprint sensor cell.

126. The method according to claim 125, wherein the value is a voltage related to a charge stored.

127. The method according to claim 125, wherein the value is a voltage related to a rate of change in a charge stored.

128. The method according to claim 122,
wherein coupling the finger to the electrical power supply comprises coupling the finger to a continuous conductive strip coupled to the electrical power supply, and wherein the continuous conductive strip surrounds the fingerprint sensor cell.

129. The method according to claim 122, further including:
placing a protective layer on the sensor cell prior to placing the finger adjacent the sensor cell.

130. The method according to claim 122, further including:
coupling the fingerprint sensor cell to a variable voltage electrical power supply;
sensing the fingerprint pattern; and
changing the voltage provided by the variable voltage power supply on the sensor cell during sensing of the fingerprint pattern.

131. A method of sensing a fingerprint pattern comprising:
placing a finger adjacent a fingerprint sensor cell;
conductively coupling the finger to an electrical power supply;
sensing the fingerprint pattern; and
changing the voltage on the finger during sensing of the fingerprint pattern,
wherein sensing the fingerprint pattern comprises measuring a value related to a charge resulting from placing the finger adjacent the fingerprint sensor cell,
wherein conductively coupling the finger to the electrical power supply comprises conductively coupling the finger to a voltage output terminal coupled to the electrical power supply, and wherein the voltage output terminal is separate from the fingerprint sensor cell.

132. The method according to claim 131, wherein the value is a voltage related to a charge stored.

133. The method according to claim 132, wherein the value is a voltage related to a rate of change in a charge stored.

134. The method according to claim 132, further including:
resetting the fingerprint sensor cell, before changing the voltage on the finger,
wherein the fingerprint sensor cell comprises a first plate and a second plate, and
wherein resetting comprises coupling and then uncoupling the first plate and the second plate.

135. The method according to claim 134, wherein resetting and changing the voltage on the finger are based on the same clock signal.

136. The method according to claim 132, further including:
coupling the first plate of the fingerprint sensor cell and the second plate of the fingerprint sensor cell, after changing the voltage on the finger.

137. The method according to claim 132, further including:
resetting the fingerprint sensor cell, after changing the voltage on the finger,
wherein the fingerprint sensor cell comprises a first plate and a second plate, and
wherein resetting comprises coupling and then uncoupling the first plate and the second plate.

138. The method according to claim 137, wherein resetting and changing the voltage on the finger are based on the same clock signal.

139. The method according to claim 132,
wherein coupling the finger to the electrical power supply comprises coupling the finger to a continuous conductive strip coupled to the electrical power supply, and
wherein the continuous conductive strip surrounds the fingerprint sensor cell.

140. The method according to claim 132, further including:
placing a protective layer on the sensor cell prior to placing the finger adjacent the sensor cell.

141. The method according to claim 132, further including:
coupling the fingerprint sensor cell to a variable voltage electrical power supply;
sensing the fingerprint pattern; and
changing the voltage provided by the variable voltage power supply on the sensor cell during sensing of the fingerprint pattern.

* * * * *